US012372519B2

(12) United States Patent
Kwon et al.

(10) Patent No.: US 12,372,519 B2
(45) Date of Patent: Jul. 29, 2025

(54) CARBENE COMPOUND, CARBENE-METAL NANOPARTICLE COMPLEX AND PREPARATION METHOD THEREOF

(71) Applicant: KOREA RESEARCH INSTITUTE OF BIOSCIENCE AND BIOTECHNOLOGY, Daejeon (KR)

(72) Inventors: Oh Seok Kwon, Daejeon (KR); Tae Joon Kang, Daejeon (KR); Seon Joo Park, Daejeon (KR); Chul Soon Park, Daejeon (KR); Kyung Ho Kim, Daejeon (KR); Jin Yeong Kim, Daejeon (KR); Ji Yeon Lee, Daejeon (KR); Chang Soo Lee, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 998 days.

(21) Appl. No.: 17/284,249

(22) PCT Filed: Oct. 10, 2019

(86) PCT No.: PCT/KR2019/013314
§ 371 (c)(1),
(2) Date: Apr. 9, 2021

(87) PCT Pub. No.: WO2020/076106
PCT Pub. Date: Apr. 16, 2020

(65) Prior Publication Data
US 2021/0356461 A1    Nov. 18, 2021

(30) Foreign Application Priority Data
Oct. 10, 2018 (KR) .................. 10-2018-0120648

(51) Int. Cl.
*G01N 33/543* (2006.01)
*C07D 235/06* (2006.01)
(Continued)

(52) U.S. Cl.
CPC ..... *G01N 33/54346* (2013.01); *C07D 235/06* (2013.01); *C07D 403/12* (2013.01); *G01N 33/54366* (2013.01); *G01N 33/553* (2013.01)

(58) Field of Classification Search
None
See application file for complete search history.

(56) References Cited

U.S. PATENT DOCUMENTS 6,025,496 A    2/2000  Herrmann et al.
7,572,912 B2   8/2009  Yam et al.
(Continued)

FOREIGN PATENT DOCUMENTS

JP    2016-536170 A    11/2016
KR    10-2000-0064700 A    11/2000
(Continued)

OTHER PUBLICATIONS

MacLeod, M. J. "PEGylated N-Heterocyclic Carbene Anchors Designed To Stabilize Gold Nanoparticles in Biologically Relevant Media." JACS. 137: 7974-7977. 2015. (Year: 2015).*
(Continued)

*Primary Examiner* — Joseph D Anthony
(74) *Attorney, Agent, or Firm* — Harness, Dickey & Pierce, P.L.C.

(57) ABSTRACT

The present invention relates to a carbene compound having substituted at the terminal polyethylene glycol (PEG) having nitrogen-containing functional groups, a carbene-metal nanoparticle complex in which the carbene compound and metal nanoparticles are bounded, a preparation method thereof, and a biosensor using same.

8 Claims, 17 Drawing Sheets

(51) Int. Cl.
 *C07D 403/12* (2006.01)
 *G01N 33/553* (2006.01)

(56) References Cited

U.S. PATENT DOCUMENTS

| | | | | |
|---|---|---|---|---|
| 8,057,780 | B2 | 11/2011 | Jang et al. | |
| 8,828,984 | B2 | 9/2014 | Che et al. | |
| 8,853,239 | B2* | 10/2014 | Himmelsbach | A61P 3/04 |
| | | | | 546/196 |
| 9,173,943 | B2* | 11/2015 | Hoshino | C07K 1/22 |
| 9,617,251 | B2* | 4/2017 | Eckhardt | A61K 31/444 |
| 11,008,291 | B2* | 5/2021 | Crudden | C07D 403/12 |
| 11,383,266 | B2 | 7/2022 | Crudden et al. | |
| 2006/0083694 | A1* | 4/2006 | Kodas | B01J 13/0095 |
| | | | | 424/490 |
| 2006/0091378 | A1 | 5/2006 | Yam et al. | |
| 2006/0100365 | A1 | 5/2006 | Tam et al. | |
| 2007/0184970 | A1* | 8/2007 | Gao | B01J 31/1633 |
| | | | | 502/170 |
| 2009/0258441 | A1* | 10/2009 | Flemming | G01N 33/553 |
| | | | | 252/301.4 R |
| 2009/0289233 | A1 | 11/2009 | Jang et al. | |
| 2011/0190506 | A1* | 8/2011 | Gao | B01J 23/745 |
| | | | | 556/146 |
| 2012/0244075 | A1* | 9/2012 | Liu | A61P 35/00 |
| | | | | 977/773 |
| 2014/0142080 | A1 | 5/2014 | Che et al. | |
| 2015/0253318 | A1* | 9/2015 | Singamaneni | G01N 33/54373 |
| | | | | 435/7.1 |
| 2016/0199875 | A1 | 7/2016 | Crudden et al. | |
| 2017/0107516 | A1 | 4/2017 | Veige et al. | |
| 2019/0169132 | A1* | 6/2019 | Crudden | G01N 21/554 |

FOREIGN PATENT DOCUMENTS

| | | |
|---|---|---|
| KR | 10-2009-0120769 A | 11/2009 |
| KR | 10-2019-0107518 A | 9/2019 |
| WO | WO-2019-083342 A1 | 5/2019 |

OTHER PUBLICATIONS

Japanese Office Action dated May 30, 2022 issued in corresponding Japanese Appln. No. 2021-520142.
Chinese Office Action dated Nov. 27, 2023 issued for corresponding Chinese Patent Application No. 201980079045.3 (with English translation).
Engel et al. "New Trends in the Functionalization of Metallic Gold: From Organosulfur Ligands to N-heterocyclic Carbenes", Chem. Soc. Rev. Apr. 18, 2017;46(8):2057-2075.
Crudden, C.M. et al., "Ultra Stable Self-Assembled Monolayers of N-heterocyclic Carbenes on Gold", Nature Chemistry 2014, vol. 6 pp. 409-414.
Ling et al., "Supracrystals of N-heterocyclic Carbene-Coated Au Nanocrystals", Chem. Mater. 2015, 27, 414-423.
MacLeod M.j et al., "PEGylated N-Heterocyclic Carbene Anchors Designed to Stabilize Gold Nanoparticles in Biologically Relevant Media" Journal of the American Chemical Society, 2015, vol. 137, pp. 7974-7977.
International Search Report PCT/ISA/210 for International Application No. PCT/KR2019/013314 dated Jan. 10, 2020.
Written Opinion PCT/ISA/237 for International Application No. PCT/KR2019/013314 dated Jan. 10, 2020.

* cited by examiner example 1  comparative example 2

CARBENE COMPOUND, CARBENE-METAL NANOPARTICLE COMPLEX AND PREPARATION METHOD THEREOF

CROSS-REFERENCE TO RELATED APPLICATIONS

This application is a national phase under 35 U.S.C. § 371 of PCT International Application No. PCT/KR2019/013314 which has an International filing date of Oct. 10, 2019, which claims priority to Korean Application No. 10-2018-0120648, filed Oct. 10, 2018, the entire contents of each of which are hereby incorporated by reference.

TECHNICAL FIELD

The present invention relates to a carbene compound, a carbene-metal nanoparticle complex, and a preparation method thereof. This application is based on and claims the benefit of priority to Korean Patent Application No. 10-2018-0120648, filed on Oct. 10, 2018, in the Korean Intellectual Property Office, the disclosure of which is incorporated herein in its entirety by reference.

BACKGROUND ART

The value of gold is very important in the industry as well as the real life, and depending on its size and shape, gold exhibits unique physical and chemical properties in various fields (semiconductor memory devices, organic chemical reaction catalysts, next generation energy, Lateral Flow Assay (LFA), biosensors, etc.). In recent years, due to the development of nano science, its application range has been more diverse according to development of gold processing methods such as gold nano manufacturing.

As mass production technology of gold nanoprobes (nanoparticles, nanorods, etc.) has been developed, the gold nanoprobes have been used for diagnosis and treatment of diseases in the bio industry, but in the gold nanoprobes, particularly, gold surface treatment technology has a very large effect on performance. For this gold surface treatment, a conventional treatment method using alkylamine, carboxylic acid (decanoic acid, citric acid, etc.), thiol, ammonium, etc. has been widely used due to advantages such as dispersibility in water or organic solvent, ease of adhesion of a bio probe part, etc.

Among them, thiol has a high binding strength to gold (Au). In addition, thiol-gold bonds are unstable on its surface under a high salt concentration solution and an acid/base solution so that agglomeration occurs, and particularly, at 60° C. or more and 0° C. or less, the agglomeration is very severe, and thus there is a serious limit on the storage of the product. For example, a gold nanoprobe as a product used in LFA for field diagnosis was released to enable aqueous dispersion by surrounding its surface with thiol, and needs to be refrigerated. However, when a bio-probe part (e.g. antibody, DNA, etc.) is immobilized on the gold nanoparticle, the product cannot be refrigerated, and as a result, there is a disadvantage that the product needs to be used immediately. In addition, due to the characteristic of the LFA product, since the product is also delivered to a lot of hot regions such as Africa, gold nanoprobes with high stability capable of withstanding a high temperature are required.

To solve the above problems, because of an advantage that the reactivity between a carbene compound and gold atoms is high and strong binding is enabled, in the related art, there was used a method for preparing carbene-gold nanoparticles by reacting imidazolium salt with gold ions to form an organic metal complex and then performing a reduction reaction (J. Am. Chem. Soc. 2015, 137, 7974-7977), but it seems that there is no uniformity in the shape or size of the gold nanoparticles. In addition, benzimidazolium salt is anion-converted into aurate ions and the organic metal complex formation and the reduction reaction are simultaneously performed at a low temperature (0.6° C.) to synthesize a uniform form of gold nanoparticles (Chem. Mater. 2015, 27, 414-423), but since the gold nanoparticles are synthesized in an organic solvent, there is a disadvantage that the gold nanoparticles are not dispersed in water and cannot be applied to biosensors. In addition, first, the conventional carbene-gold nanoparticles have no functional group at a terminal, so that it is impossible to be applied to the biosensors and the like.

PRIOR ART (Patent Document 1) US Laid-open Patent Publication No. 2006/0100365 (May 11, 2006)

DISCLOSURE

Technical Problem

An object of the present invention is to provide a carbene-gold nanoparticle complex with chemical and physical stability even in various environments of a high-concentration salt solution, strong acid or strong base, and high temperature and ultra-low temperature, by synthesizing a carbene compound including functional groups at a terminal to stabilize the surfaces of carbene-metal nanoparticles, so as to be used to fields of biosensors such as LFA and the like.

Technical Solution

The present invention provides a carbene compound represented by the following Chemical Formula 1 or 2 substituted with polyethylene glycol (PEG) having nitrogen-containing functional groups at a terminal:

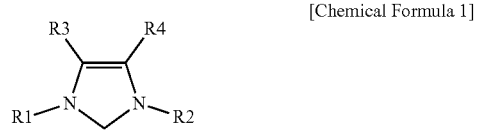

[Chemical Formula 1]

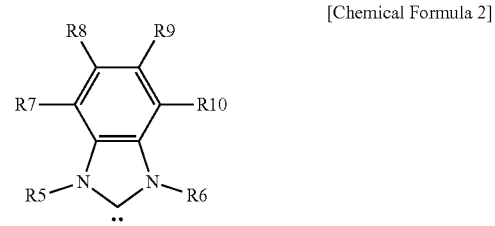

[Chemical Formula 2]

In Chemical Formulas 1 and 2 above,

R1, R2, R5 and R6 are equal to or different from each other, and each independently hydrogen, an alkyl group having 1 to 20 carbon atoms, a cycloalkyl group having 3 to 20 carbon atoms, an aryl group having 6 to 30 carbon atoms, or a heteroaryl group having 2 to 30 carbon atoms, R3, R4, R7, R8, R9 and R10 are equal to or different from each other, and each independently hydrogen, an alkyl group having 1 to 20 carbon atoms, a cycloalkyl group having 3 to 20 carbon atoms, an aryl group having 6 to 30 carbon atoms, a heteroaryl group having 2 to 30 carbon atoms, or a structure represented by the following Chemical Formula 3, or two or more substituents adjacent to each other in R7 to R10 bind to each other to form a hydrocarbon ring, at least one of R3 and R4 is a structure represented by the following Chemical Formula 3, at least one of R7 to R10 is a structure represented by the following Chemical Formula 3, or when two or more substituents adjacent to each other in R7 to R10 bind to each other to form a hydrocarbon ring, at least one of hydrogens binding to carbons forming the hydrocarbon ring is substituted with the structure represented by the following Chemical Formula 3,

[Chemical Formula 3]

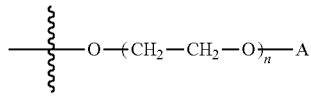

in Chemical Formula 3 above, n is an integer of 1 to 30 as the number of repeated units in parentheses, and A is an aromatic hydrocarbon group having 1 to 20 carbon atoms containing nitrogen (N) atoms or an aliphatic hydrocarbon group having 2 to 30 carbon atoms containing nitrogen (N) atoms.

Further, the present invention also provides a carbene-metal nanoparticle complex in which the carbene compound described above binds to metal nanoparticles.

The present invention provides a preparation method of a carbene-metal nanoparticle complex comprising mixing metal nanoparticles with polyethylene glycol containing a thiol group; and mixing the carbene compound described above with the metal nanoparticles bound with the polyethylene glycol containing the thiol group.

Further, the present invention provides a biosensor comprising the carbene-metal nanoparticle complex described above.

Advantageous Effects

According to the present invention, since the carbene compound has excellent stability, in the carbene-metal nanoparticle complex prepared by binding the carbene compound to metal, as compared with conventional metal nanoprobes, the carbene compound is not easily separated from the metal nanoparticles even in various types of solvents and various ranges of pH or temperature. Therefore, the carbene-metal nanoparticle complex of the present invention is used to more firmly immobilize a bio-probe part (biomaterial) and may be usefully applied to biosensors and the like.

BEST MODE

Figure 1:
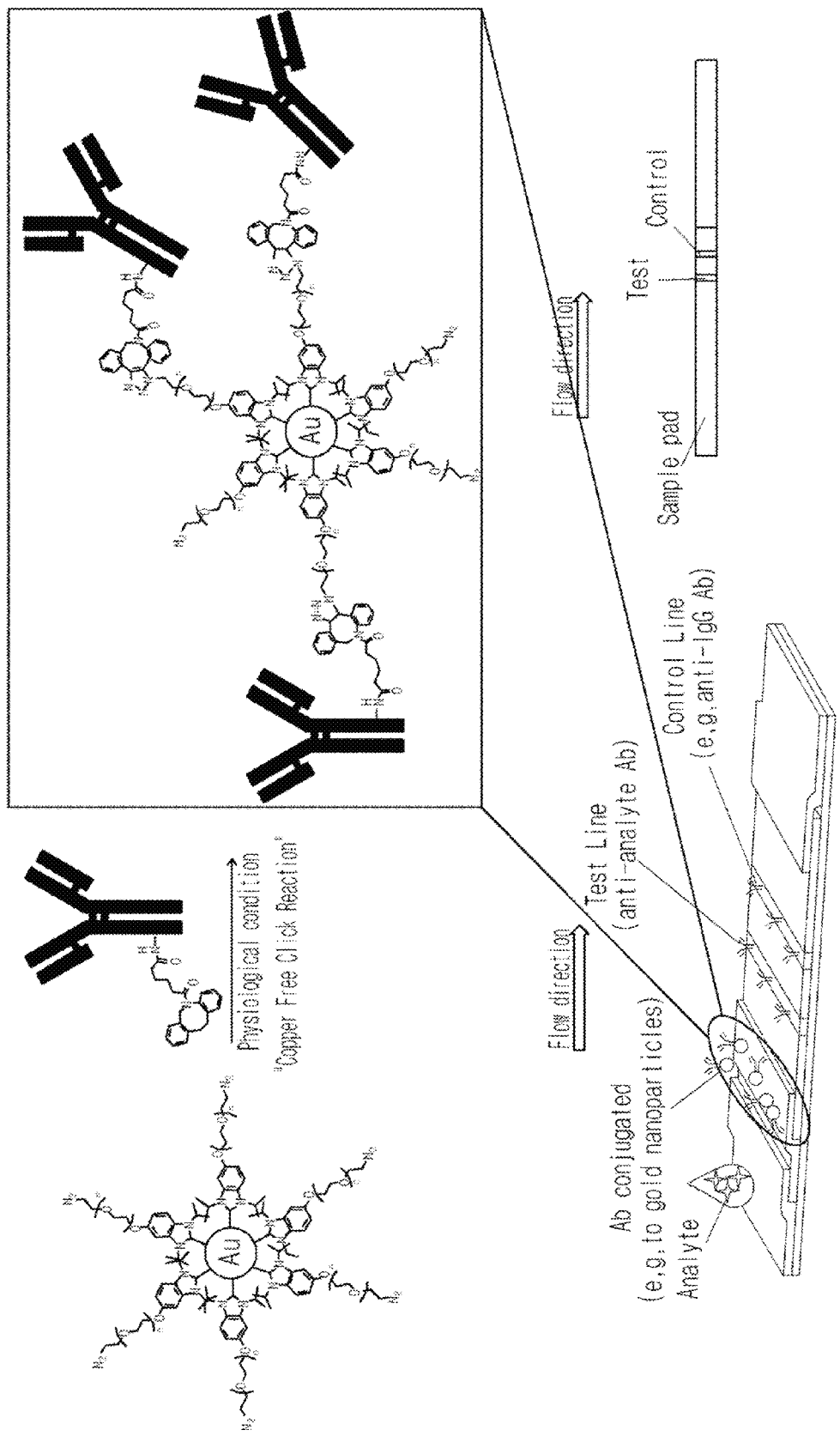
FIG. 1 is a schematic diagram illustrating LFA using a carbene-gold nanoparticle complex according to an embodiment of the present invention.

Hereinafter, the present invention will be described in detail.

1. Carbene Compound

The present invention provides a carbene compound represented by the following Chemical Formula 1 or 2 substituted with polyethylene glycol (PEG) having nitrogen-containing functional groups at a terminal.

The carbene compound may be prepared by introducing polyethylene glycol (PEG) substituted with nitrogen-containing functional groups to a terminal.

The carbene compound introduces a polyethylene glycol group to a terminal site to increase aqueous dispersibility, and introduces nitrogen-containing functional groups to the polyethylene glycol terminal to be functionalized to facilitate adhesion of a bio-probe part (e.g. antibody, DNA, aptamer, primer, etc.) to the nitrogen-containing functional groups through a click reaction below. Accordingly, in LFA and the like, unlike that the bio-probe part is typically bound by electrostatic attraction between metal nanoparticles, there is an advantage that the bio-probe part may be immobilized with strong chemical covalent bonds through the click reaction.

The nitrogen-containing functional group may be azide, phthalimide or amine.

The R1, R2, R5 and R6 may be equal to or different from each other and each independently hydrogen, an alkyl group having 1 to 20 carbon atoms, or an aryl group having 6 to 30 carbon atoms.

The R1, R2, R5 and R6 may be equal to or different from each other and each independently hydrogen or an alkyl group having 1 to 20 carbon atoms.

The R1, R2, R5 and R6 may be equal to or different from each other and each independently hydrogen, isopropyl, or benzyl.

At least one of the R1 and R2 and at least one of the R5 and R6 may be equal to or different from each other and each independently an alkyl group having 1 to 20 carbon atoms or an aryl group having 6 to 30 carbon atoms.

At least one of the R1 and R2 and at least one of the R5 and R6 may be equal to or different from each other and each independently isopropyl or benzyl.

The R3, R4, R7, R8, R9 and R10 are equal to or different from each other, and each independently hydrogen, an alkyl group having 1 to 20 carbon atoms, a cycloalkyl group having 3 to 20 carbon atoms, an aryl group having 6 to 30 carbon atoms, a heteroaryl group having 2 to 30 carbon atoms, or a structure represented by the following Chemical Formula 3, or two or more substituents adjacent to each other in R7 to R10 bind to each other to form a hydrocarbon ring.

The R3, R4, R7, R8, R9 and R10 are equal to or different from each other, and each independently hydrogen or a structure represented by the following Chemical Formula 3, or two or more substituents adjacent to each other in R7 to R10 bind to each other to form a hydrocarbon ring.

When the two or more substituents adjacent to each other in R7 to R10 bind to each other to form the hydrocarbon ring, at least one of hydrogens binding to carbons forming the hydrocarbon ring may be substituted with the structure represented by Chemical Formula 3.

At least one of R3 and R4 may be the structure represented by Chemical Formula 3. In addition, a least one of R7 to R10 may be the structure represented by Chemical Formula 3.

The n may be an integer of 1 to 30 as the number of repeated units in parentheses, and preferably 1 to 10. When the n is less than 1, the aqueous dispersibility of the carbene compound is lowered, and when the n is more than 30, a distance between the bio-probe parts is increased due to a long chain of polyethylene glycol, and thus, the bio sensing efficiency rather decreases.

The A is an alkyl group having 1 to 20 carbon atoms containing nitrogen (N) atoms or a heteroaryl group having 2 to 30 carbon atoms containing nitrogen (N) atoms. Specifically, the A may be azide, phthalimide or amine.

In the present invention, the "adjacent" group may mean a substituent substituted to an atom linked directly to an atom substituted with the corresponding substituent, a substituent that is located stereoscopically closest to the corresponding substituent, or another substituent substituted to an atom substituted with the corresponding substituent. For example, it will be interpreted that two substituents substituted in ortho sites in a benzene ring and two substituents substituted to the same carbon in an aliphatic ring are groups "adjacent" to each other.

The alkyl group may be a linear or branched chain, and may have 1 to 20 carbon atoms, preferably 1 to 10 carbon atoms. More preferably, the alkyl group may have 1 to 6 carbon atoms. Specific examples of the alkyl group include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl methyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, ishexyl, 4-methylhexyl, 5-methylhexyl, benzyl, etc., but are not limited thereto.

The cycloalkyl group may have 3 to 20 carbon atoms, preferably 3 to 10 carbon atoms. Specific examples of the cycloalkyl group include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, etc., but are not limited thereto.

The aryl group may have 6 to 30 carbon atoms, preferably 6 to 10 carbon atoms. The aryl group may be a monocyclic aryl group or a polycyclic aryl group. Specific examples of the monocyclic aryl group include a phenyl group, a biphphenyl group, a terphenyl group, etc., and the specific examples of the polycyclic aryl group include a naphthyl group, an anthracenyl group, a phenanthyl group, a pyrenyl group, a perylenyl group, a chrysenyl group, a fluorenyl group, a triphenylene group, etc., but are not limited thereto.

The heteroaryl group may be an aromatic ring group including one or more selected from N, O, P, S, Si and Se as a heteroatom, and may have 2 to 30 carbon atoms, preferably 2 to carbon atoms. Specific examples of the heteroaryl group include a thiophene group, a furan group, a pyrrole group, an imidazole group, a triazole group, an oxazole group, an oxadiazole group, a triazole group, a pyridyl group, a pyrimidyl group, a triazine group, a triazole group, an acryldyl group, a quinolinyl group, a quinazoline group, a quinoxalinyl group, a phtalazyrinyl group, an isquinoline group, an indole group, a carbazole group, a benzoxazole group, a benzimidazoline group, a benzothiazole group, a benzocarbazole group, a benzothiophene group, a dibenzothiophene group, a benzofuranyl group, etc., but are not limited thereto.

In addition, the alkyl group, the cycloalkyl group, the aryl group, the heteroaryl group, or the hydrocarbon ring may be substituted or unsubstituted with an alkyl group, a cycloalkyl group, an aryl group or a heteroaryl group again.

2. Carbene-Metal Nanoparticle Complex and Preparation Method Thereof

The present invention also provides a carbene-metal nanoparticle complex in which the carbene compound described above binds to metal nanoparticles.

The particle diameter of the metal nanoparticle may be 1 nm to 40 nm. When the particle diameter of the metal nanoparticle is less than 1 nm, it is difficult to introduce a required level of carbene compound to the surface of the metal nanoparticle, and thus, the efficiency as a biosensor is deteriorated. When the particle diameter of the metal nanoparticle is more than 40 nm, the carbene-metal nanoparticle complex is not uniform, and thus, the efficiency and reproducibility of the biosensor may be deteriorated. That is, if the particle diameter of the metal nanoparticle exceeds 40 nm, a possibility that the agglomeration of the metal nanoparticles may occur is increased only by a small change in environment.

The metal nanoparticle may be any one selected from the group consisting of copper (Cu), cobalt (Co), bismuth (Bi), silver (Ag), aluminum (Al), gold (Au), hafnium (Hf), chromium (Cr), indium (In), manganese (Mn), molybdenum (Mo), magnesium (Mg), nickel (Ni), niobium (Nb), lead (Pb), palladium (Pd), platinum (Pt), rhenium (Re), rhodium (Rh), antimony (Sb), tantalum (Ta), titanium (Ti), tungsten (W), vanadium (V), zirconium (Zr), zinc (Zn), iron (Fe), and mixtures thereof (e.g., bimetallic nanoparticles). Preferably, the metal may be gold (Au) when considering stability and crystallizability in various environments of the biosensor to which the carbene-metal nanoparticle complex is applied and a binding force between the carbene compound and the surfaces of the metal nanoparticles.

Figure 16:
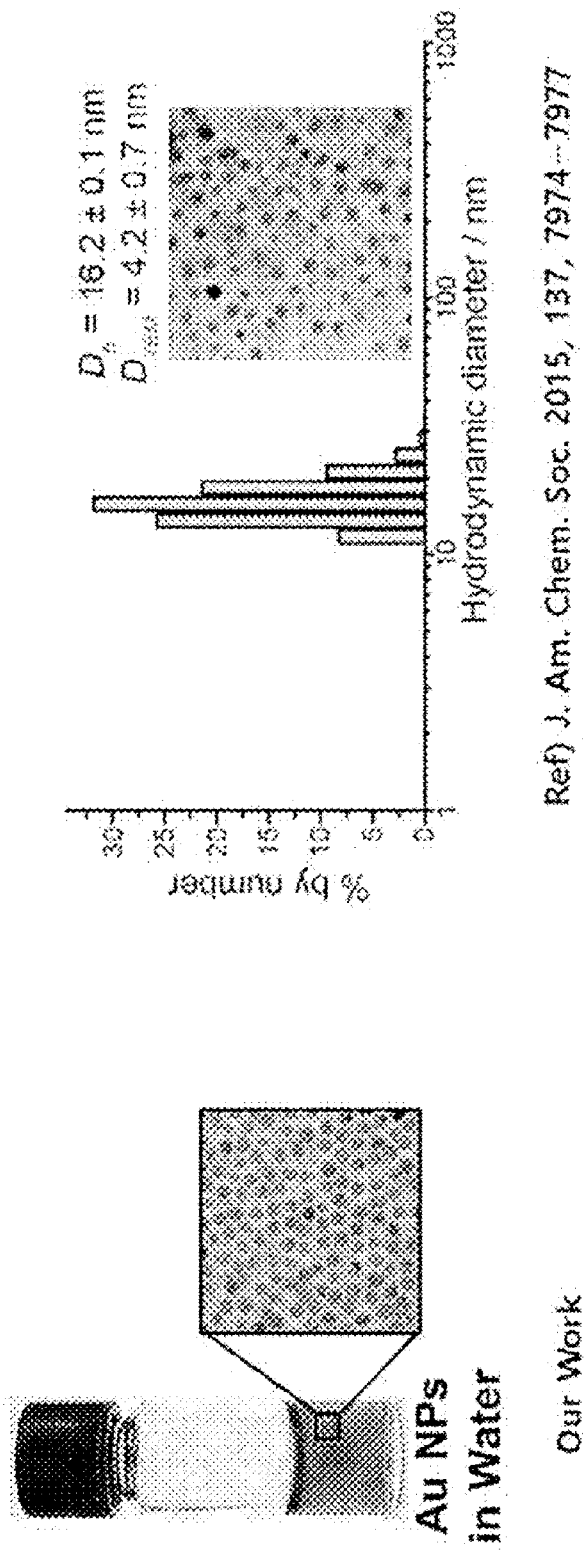
FIG. 16 is a diagram illustrating a TEM image of a carbene-metal nanoparticle complex according to an embodiment of the present invention.

The carbene-metal nanoparticle complex may have a uniform form, as illustrated in a TEM image of FIG. 16, and the aqueous dispersibility becomes excellent because the carbene-metal nanoparticle complex has the uniform form.

Further, the present invention provides a preparation method of a carbene-metal nanoparticle complex comprising preparing sulfur-metal nanoparticles by mixing polyethylene glycol containing a thiol group at one terminal and a nitrogen-containing functional group at the other terminal with metal nanoparticles, and mixing the sulfur-metal nanoparticles with the carbene compound described above.

Specifically, in the case of mixing the polyethylene glycol containing the thiol group at the one terminal and the nitrogen-containing functional group at the other terminal with the metal nanoparticles, the polyethylene glycol including the nitrogen-containing functional group at the terminal may be introduced to the surface of the metal nanoparticles, by mediating a metal-sulfur bond of sulfur of the thiol group on the metal surface. When the above-described carbene compound according to the present invention is introduced to the sulfur-metal nanoparticles formed above, while the metal-sulfur bond present on the surface of the metal nanoparticles is substituted with a metal-carbene bond, finally, the carbene-metal nanoparticle complex may be formed.

Figure 17:
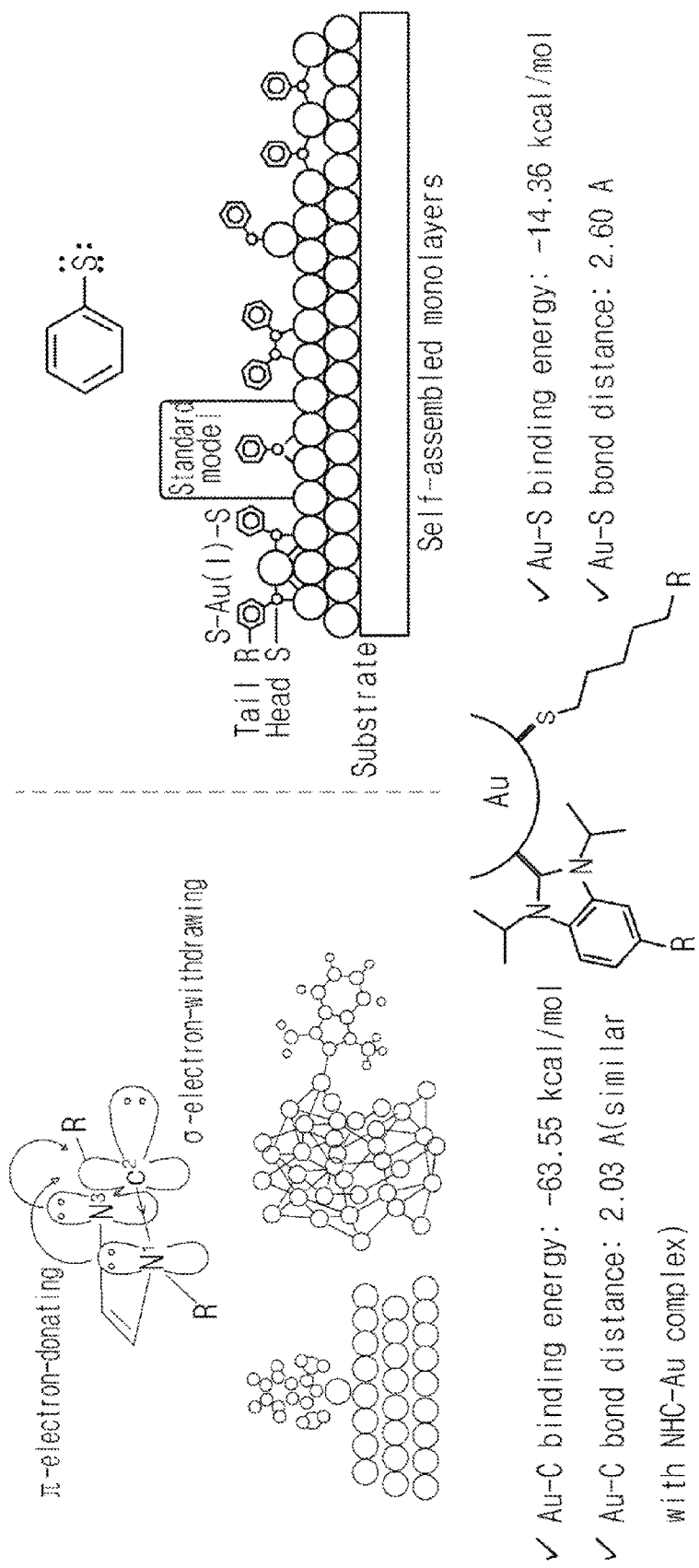
FIG. 17 is a diagram of comparing binding energy/bond distances of a gold-sulfur bond and a gold-carbene bond.

At this time, the reaction for substituting the metal-sulfur bond present on the surface of the metal nanoparticles with the metal-carbene bond may occur at room temperature (20° C. to 30° C.). Since the binding force of the metal-carbene bond is stronger than that of the metal-sulfur bond as known above, the substitution reaction may occur even only when left at room temperature for 1 to 10 hours. Particularly, referring to FIG. 17, when the metal is gold (Au), the intensity of the gold-carbene bond (binding energy: −63.55 Kcal/mol, bond distance: 2.03 Å) is stronger than that of the gold-sulfur bond (binding energy: −14.36 Kcal/mol, bond distance: 2.60 Å), and thus, as described above, the metal-sulfur bond may be easily substituted with the gold-carbene bond even at room temperature (see Chem. Soc. Rev. 2017 Apr. 18; 46(8):2057-2075).

Since the nitrogen group is exposed to the terminal as described above, the carbene-metal nanoparticle complex has an advantage of more easily bonding the bio-probe part (biomaterial). In particular, unlike the metal-sulfur bond, due to the stability of the metal-carbene bond, even in various environments of a high-concentration salt condition, a strong acid or weak base condition, and high temperature and ultra low temperature, the metal-carbene bond is maintained, so that there is an effect that the agglomeration of the carbene-metal nanoparticle complex may not occur.

3. Biosensor

The present invention provides a biosensor comprising the carbene-metal nanoparticle complex described above.

The biosensor, in particular, the color thereof is changed by a particle size, a material, a shape, and a surrounding environment of the metal nanoparticles, and as a result, the biosensor may be a nano biosensor using a changed surface plasmon band of the metal nanoparticles, but is not limited thereto. The biosensor may be a lateral flow assay (LFA) diagnostic kit for field diagnosis manufactured to be easily portable, and in addition, a surface-enhanced raman spectroscopy (SERS)-based biosensor, a dark field-based biosensor, and the like may be applied.

At this time, it is important to immobilize a bio-probe part (e.g. antibody, DNA, aptamer, primer, etc.), which specifically binds to a biomaterial to be analyzed, to a substrate or metal nanoparticle.

In the biosensor, the carbene-metal nanoparticle complex of the present invention may serve to immobilize the bio-probe part. Specifically, the carbene-metal nanoparticle complex of the present invention includes the nitrogen-containing functional group at the terminal, so that the bio-probe part (e.g., antibody, DNA, aptamer, primer, etc.) may adhere to the nitrogen-containing functional group using a click reaction. Accordingly, generally, unlike that the bio-probe part binds to the metal nanoparticle by electrostatic attraction, since the bio-probe part may be immobilized to the metal nanoparticle by a stronger chemical bond, when the bio-probe part is applied to fields such as a biosensor and the like, there are advantages of enhancing the applicability to various environments in addition to the excellent storability and ease of storage of the product.

Hereinafter, the present invention will be described in more detail with reference to preferred Examples.

However, these Examples are to describe the present invention in more detail, and the scope of the present invention is not limited thereto.

<PREPARATION EXAMPLES> PREPARATION OF CARBENE COMPOUND

Preparation Example 1

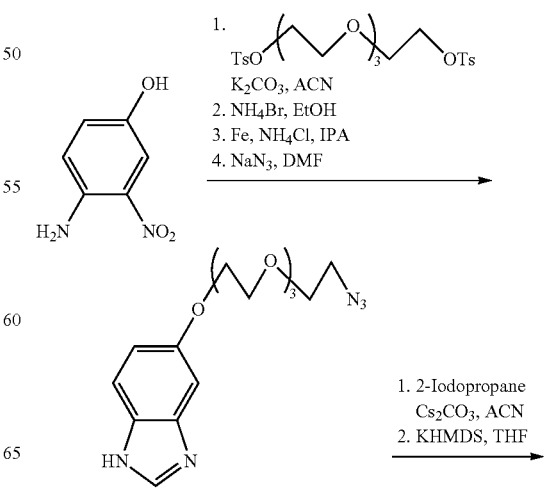

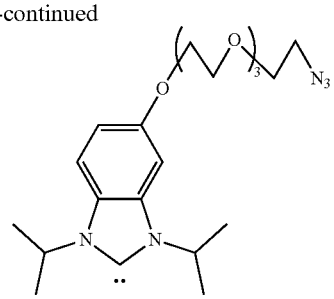

According to Reaction Formula above, carbene compound 1 was prepared.

Figure 11:
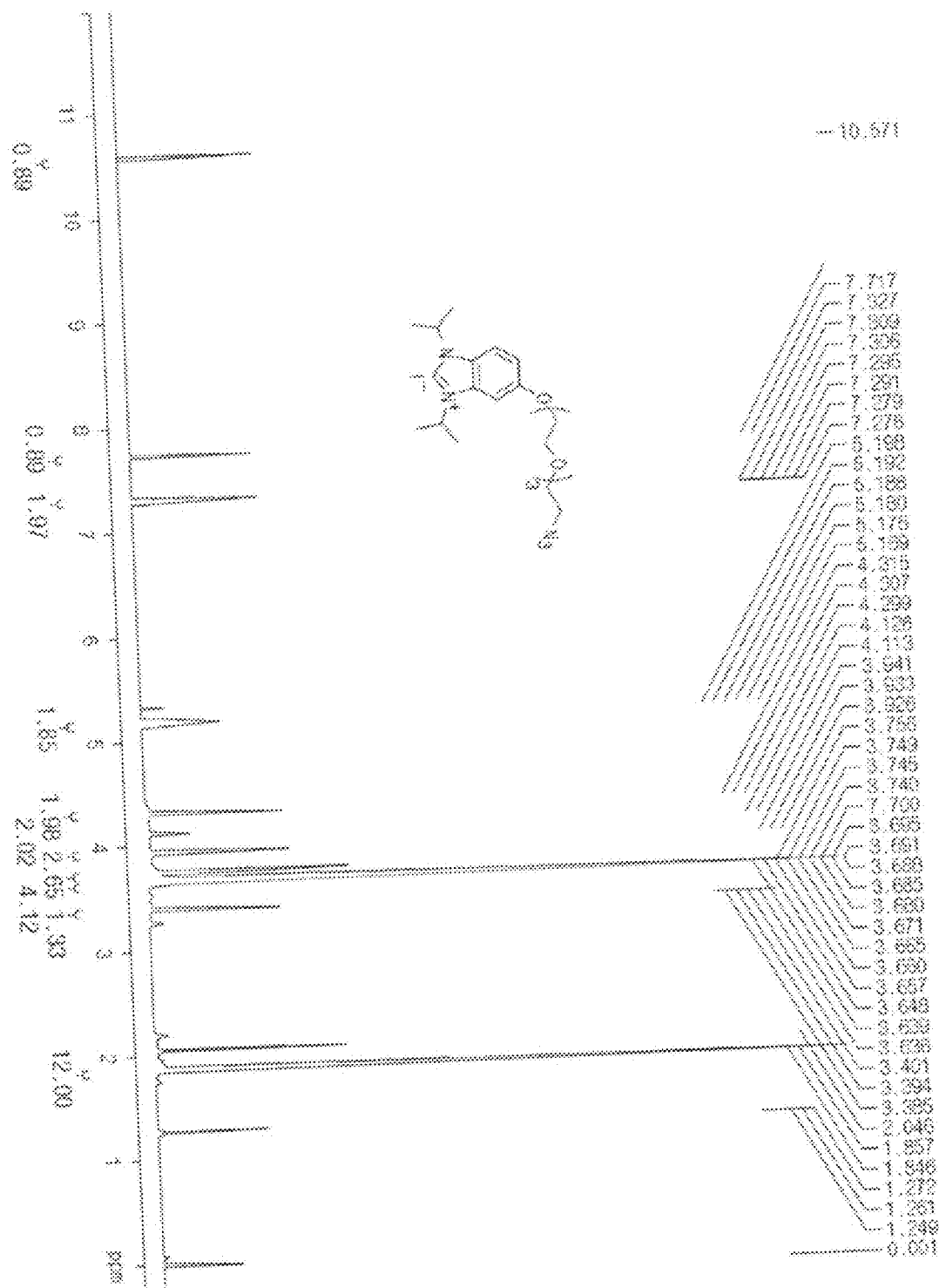
FIG. 11 is a diagram illustrating $^1$H-NMR spectra of a carbene compound prepared according to Preparation Example 1 of the present invention.

FIG. 11 illustrated a result of ¹H-NMR analysis of carbene compound 1.

Preparation Example 2

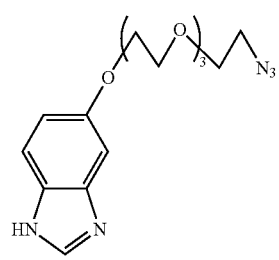

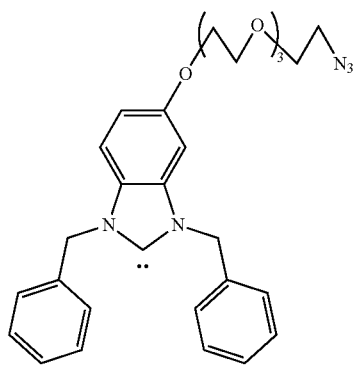

According to Reaction Formula above, carbene compound 2 was prepared.

Preparation Example 3

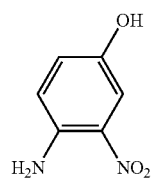

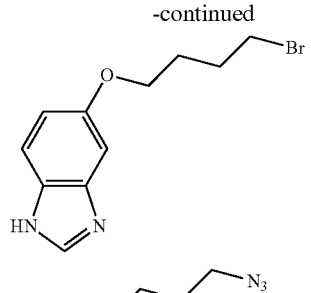

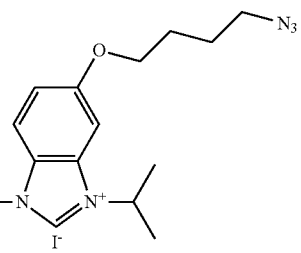

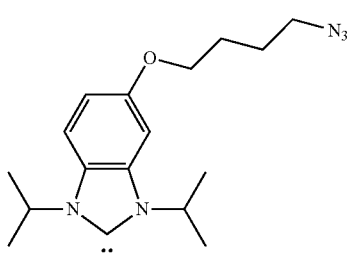

According to Reaction Formula above, carbene compound 3 was prepared.

Figure 12:
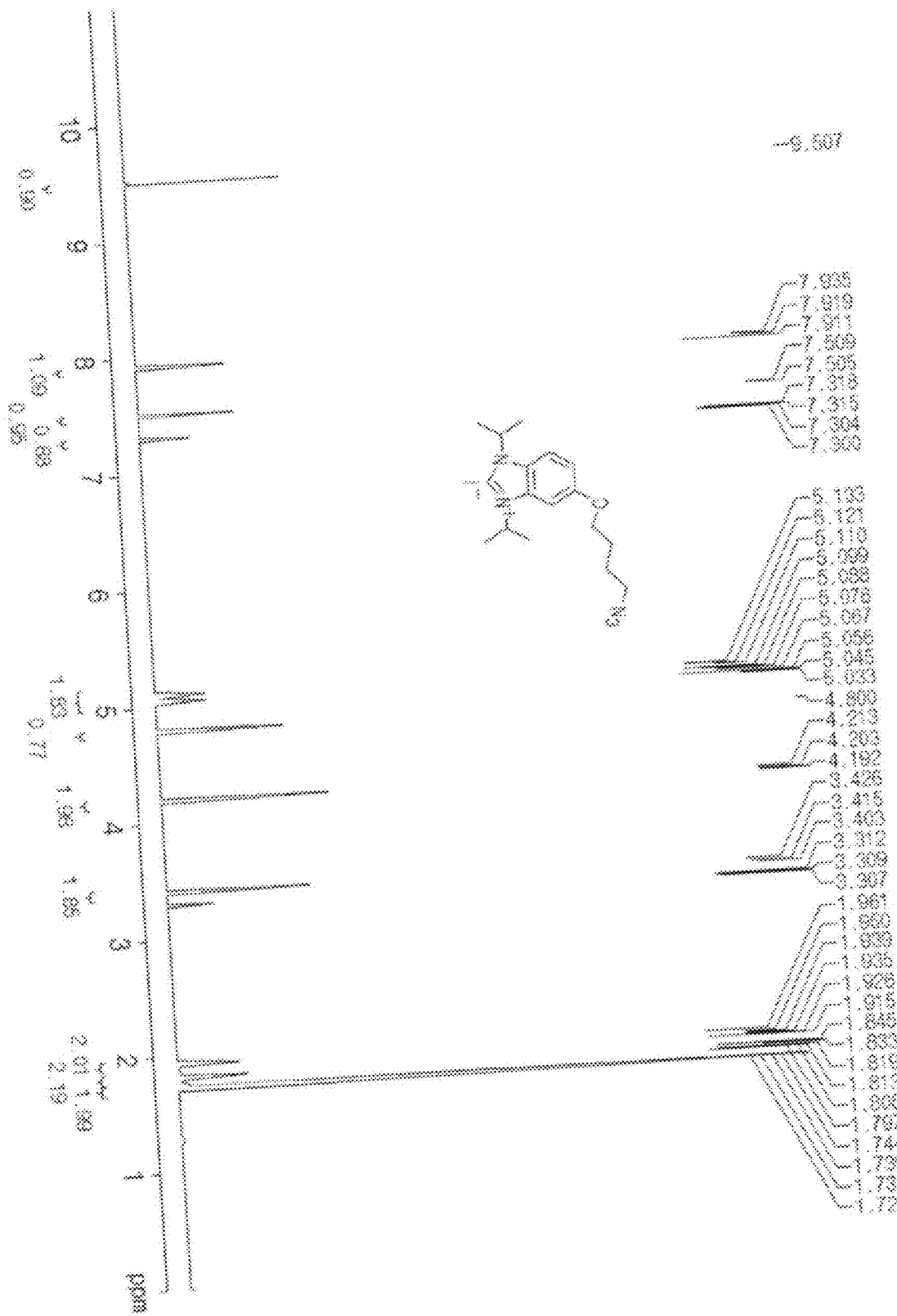
FIG. 12 is a diagram illustrating $^1$H-NMR spectra of a carbene compound prepared according to Preparation Example 3 of the present invention.

FIG. 12 illustrated a result of ¹H-NMR analysis of carbene compound 3.

Preparation Example 4

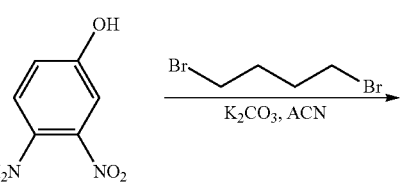

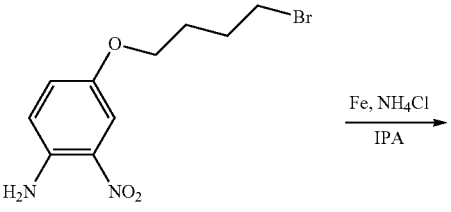

Figure 13:
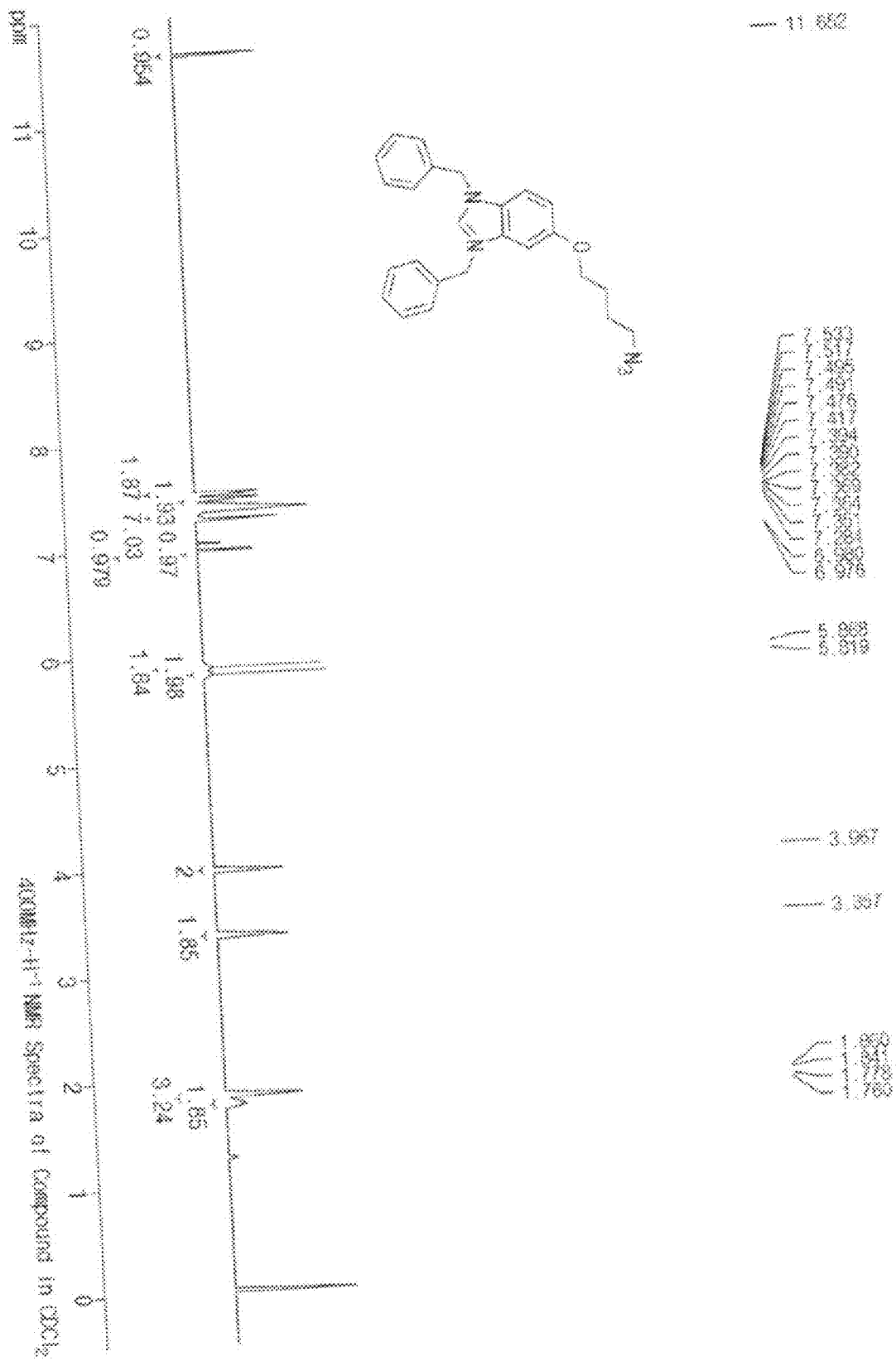
FIG. 13 is a diagram illustrating $^1$H-NMR spectra of a carbene compound prepared according to Preparation Example 4 of the present invention.
Figure 14:
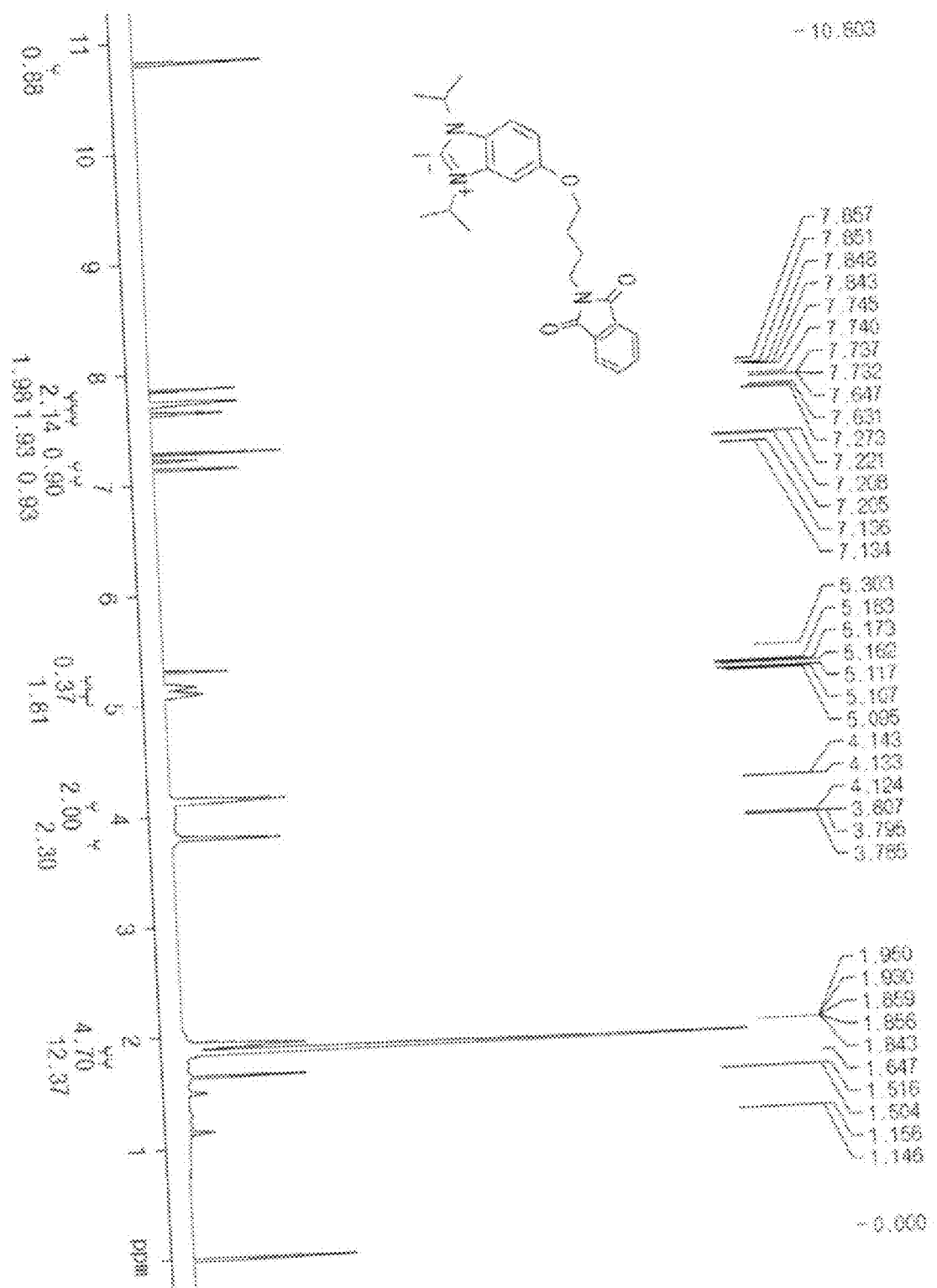
FIG. 14 is a diagram illustrating $^1$H-NMR spectra of a carbene compound prepared according to Preparation Example 5 of the present invention.

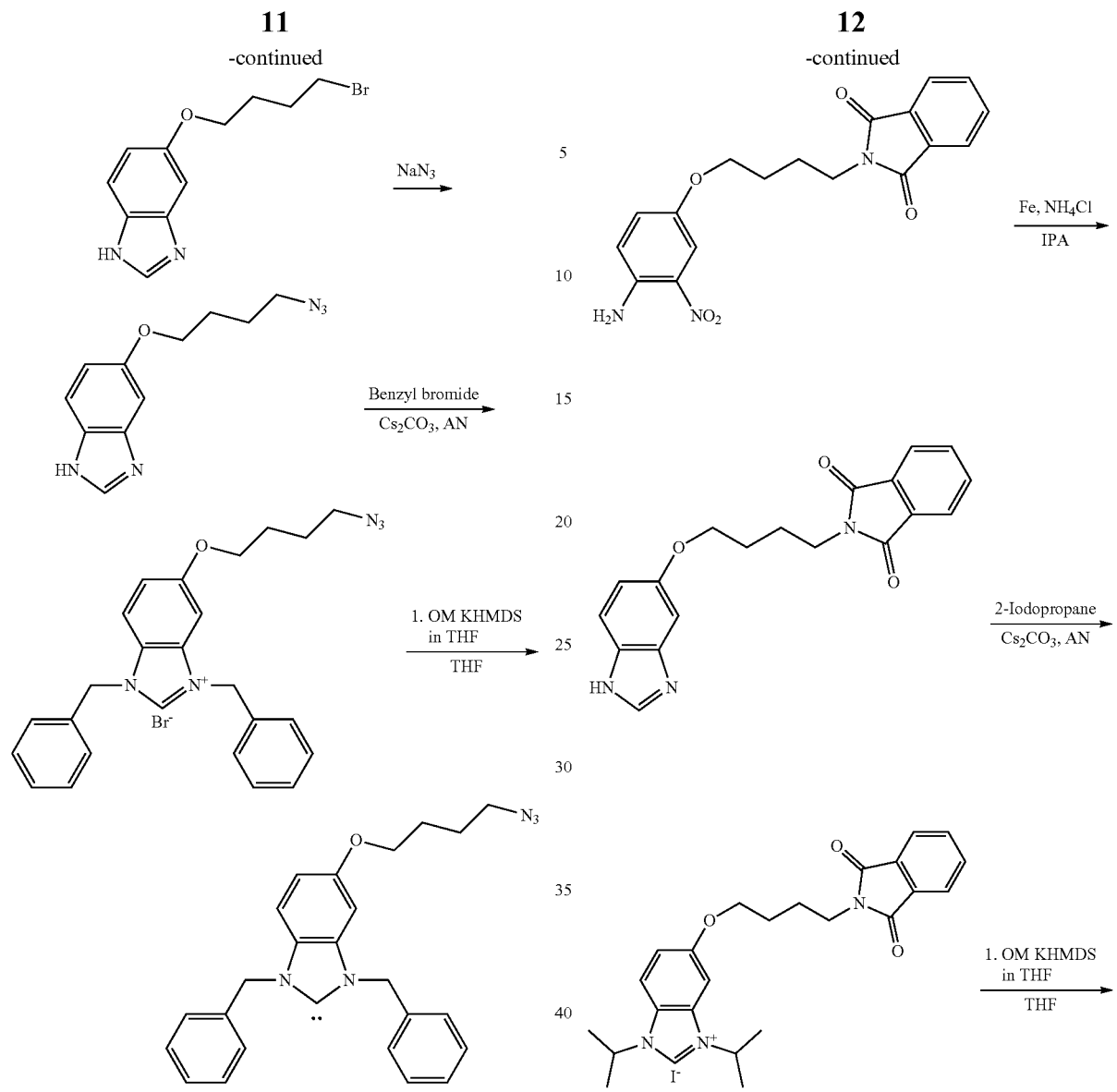
According to Reaction Formula above, carbene compound 4 was prepared.
FIG. 13 illustrated a result of $^1$H-NMR analysis of carbene compound 4.
Preparation Example 5
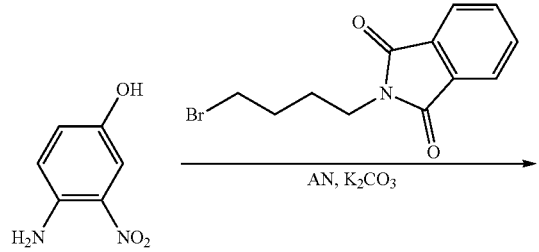
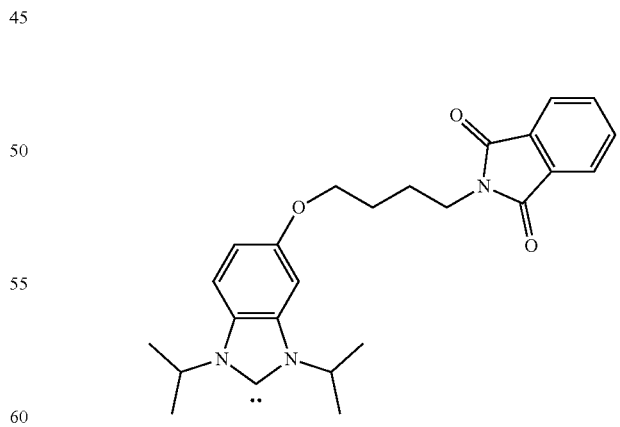
According to Reaction Formula above, carbene compound 5 was prepared.
FIG. 14 illustrated a result of $^1$H-NMR analysis of carbene compound 5.

Figure 15:
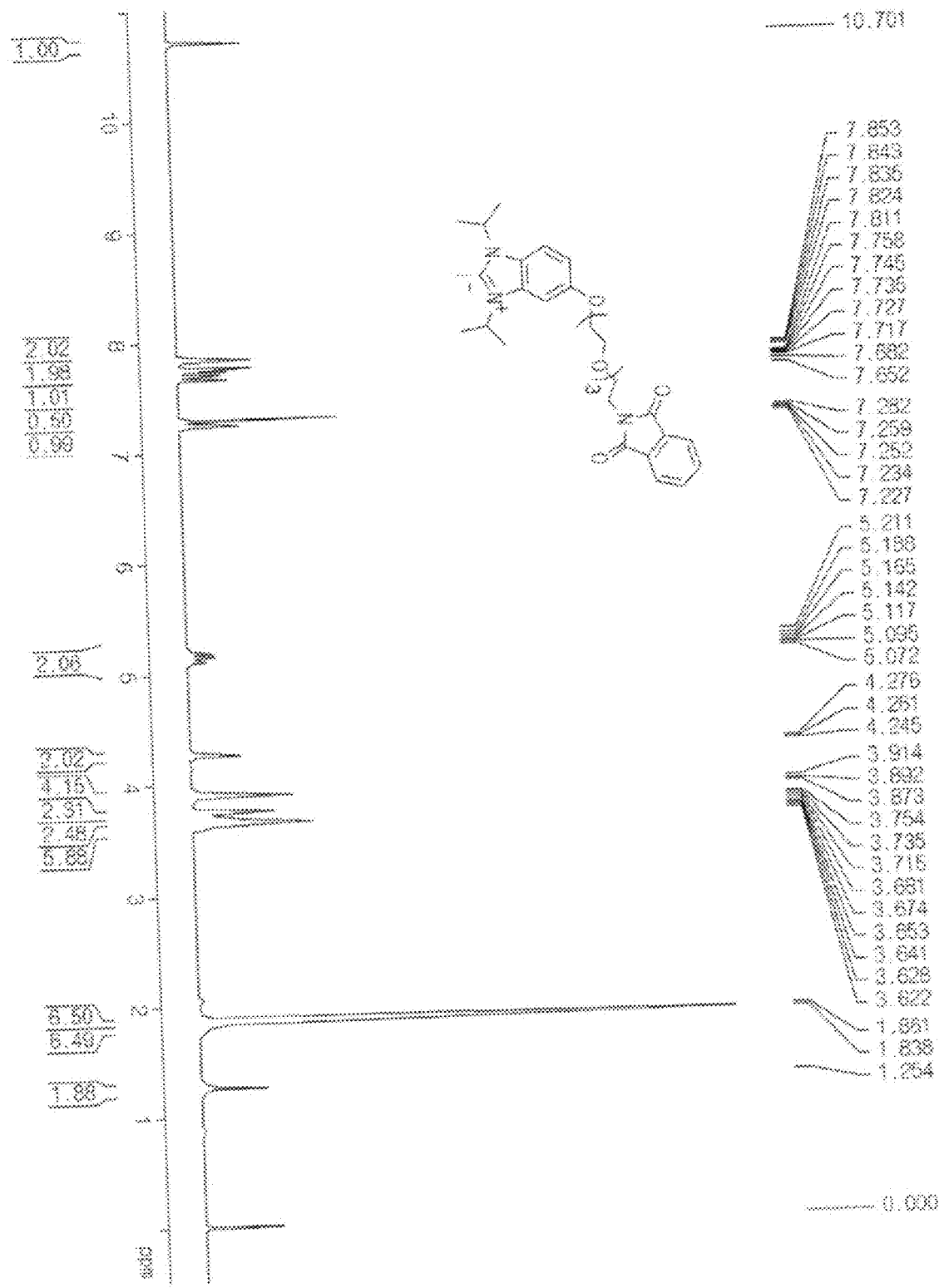
FIG. 15 is a diagram illustrating $^1$H-NMR spectra of a carbene compound prepared according to Preparation Example 6 of the present invention.

Preparation Example 6
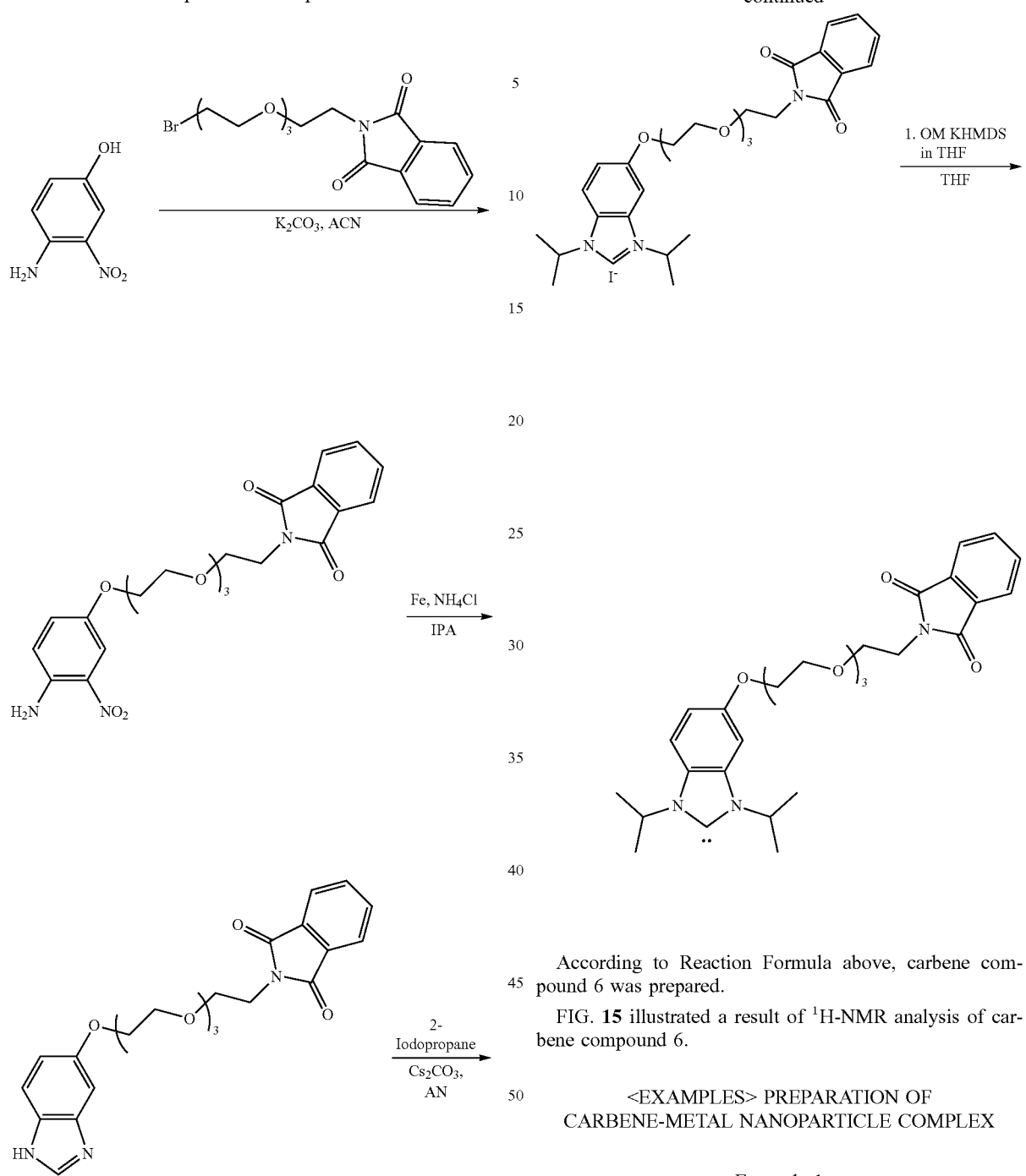
According to Reaction Formula above, carbene compound 6 was prepared.
FIG. 15 illustrated a result of $^1$H-NMR analysis of carbene compound 6.
<EXAMPLES> PREPARATION OF CARBENE-METAL NANOPARTICLE COMPLEX
Example 1
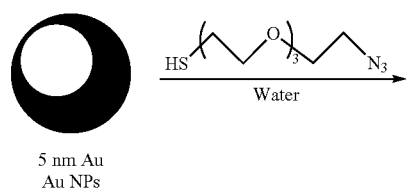

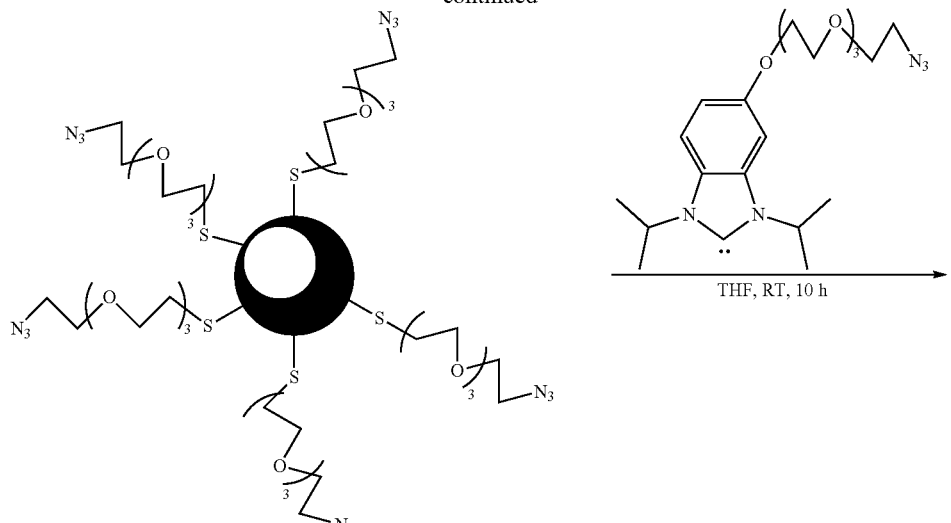

Au NPs Thiol

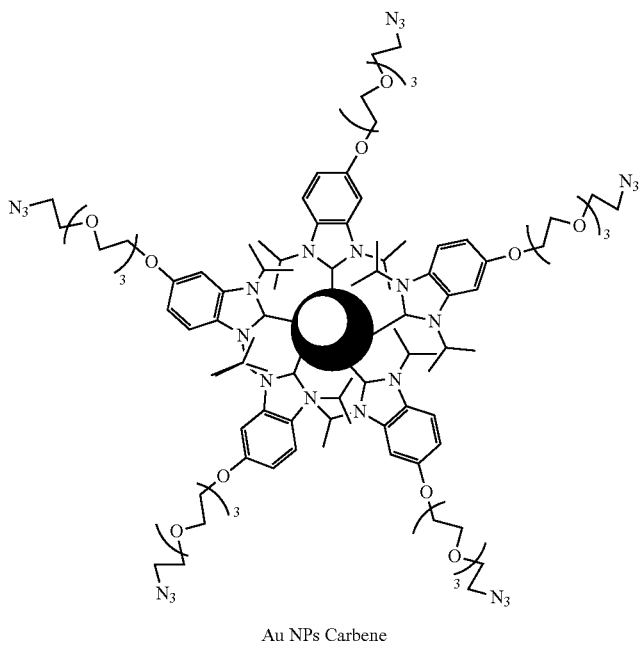

Au NPs Carbene

First, a thiol-PEG compound in which azide was introduced to a terminal was added into gold nanoparticles dispersed in an organic solvent to prepare a gold nanoparticle complex (Au NPs Thiol) by gold-sulfur bonds.

Thereafter, carbene compound 1 prepared in Preparation Example 1 was added, and the gold-sulfur bond was substituted with the gold-carbene bond to prepare a carbene-gold nanoparticle complex (Au NPs Carbene).

Comparative Example 1

A gold nanoparticle complex such as the following structure was prepared.

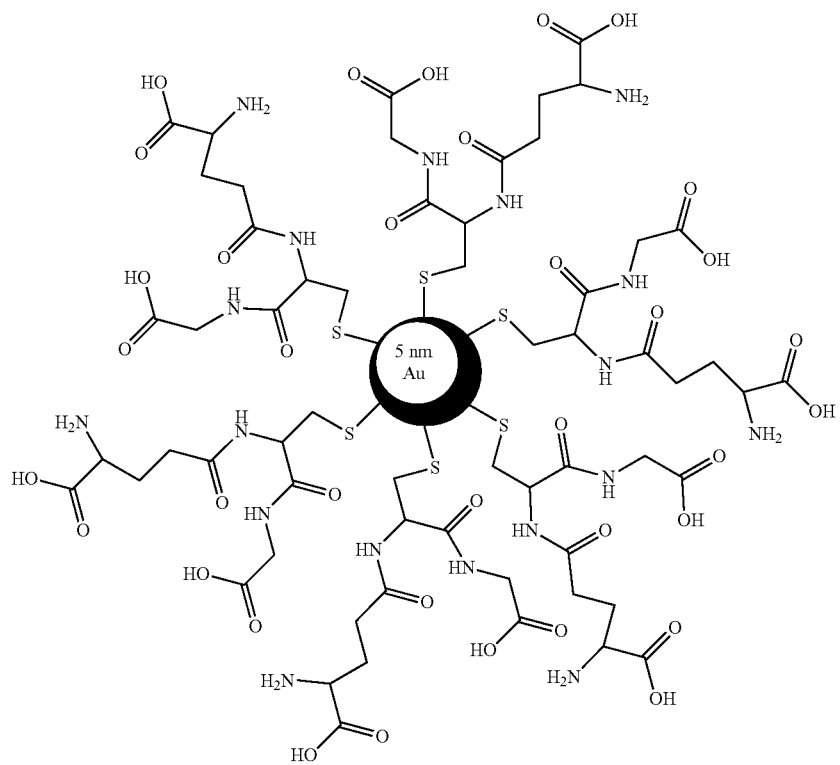

Comparative Example 2

A gold nanoparticle complex such as the following structure was prepared.

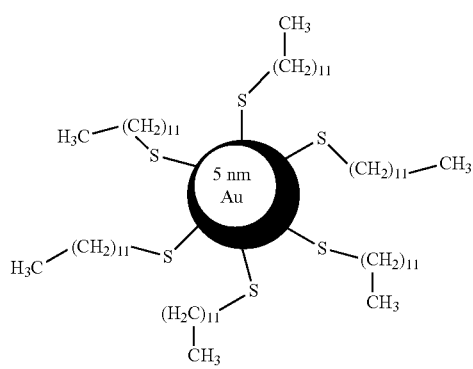

EXPERIMENTAL EXAMPLES

<Experimental Example 1> pH Stability Experiment

Figure 2:
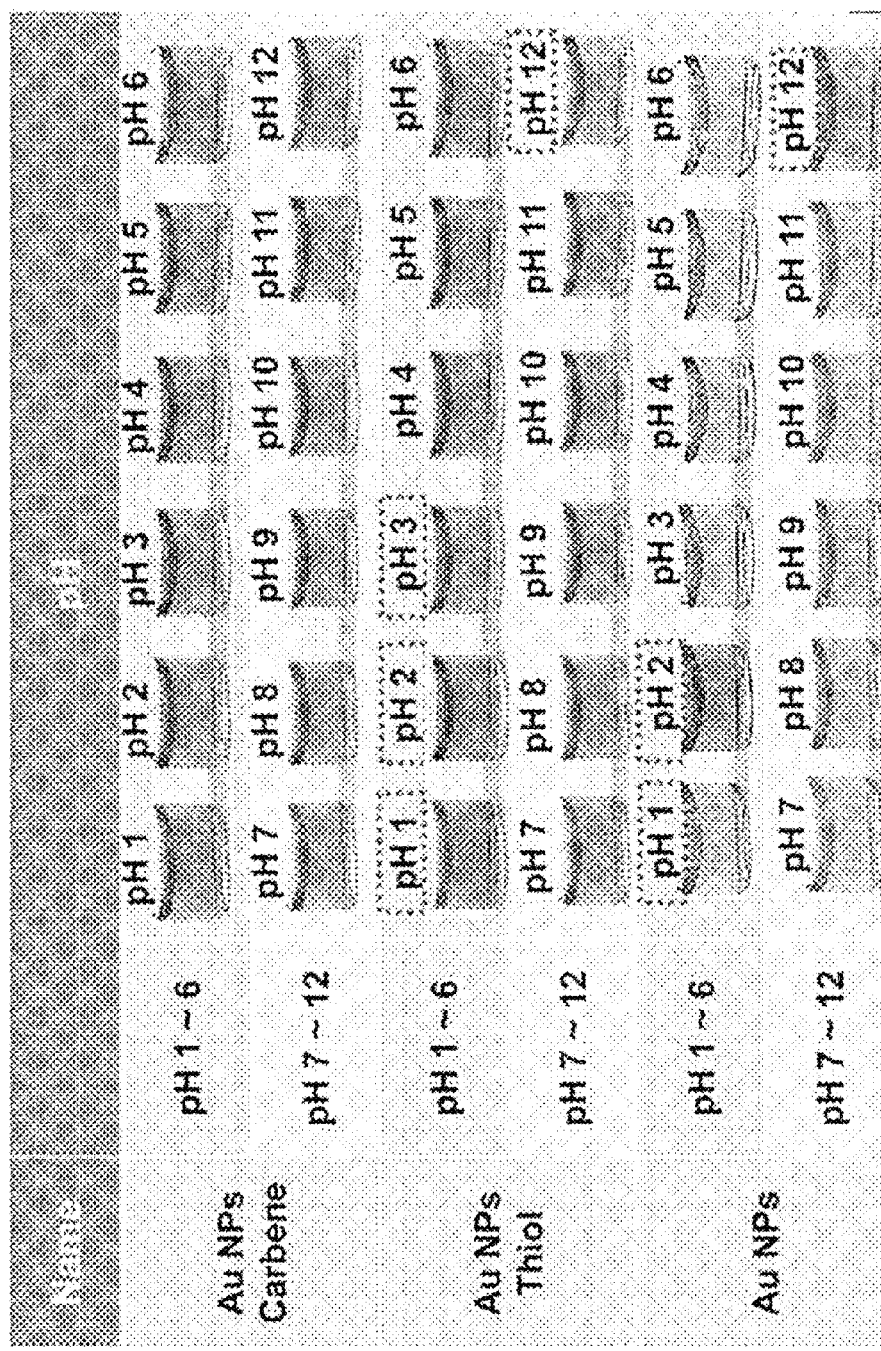
FIG. 2 is a diagram illustrating an experimental result of pH stability according to Experimental Example 1 of the present invention.

Solutions of pH 1 to 12 were prepared, respectively, and added with the carbene-gold nanoparticle complex (Au NPs Carbene) and the gold nanoparticle complex (Au NPs Thiol) of Example 1, and then changes in colors of the solutions were observed, and the result was shown in FIG. 2.

<Experimental Example 2> Salt Stability Experiment

Figure 3:
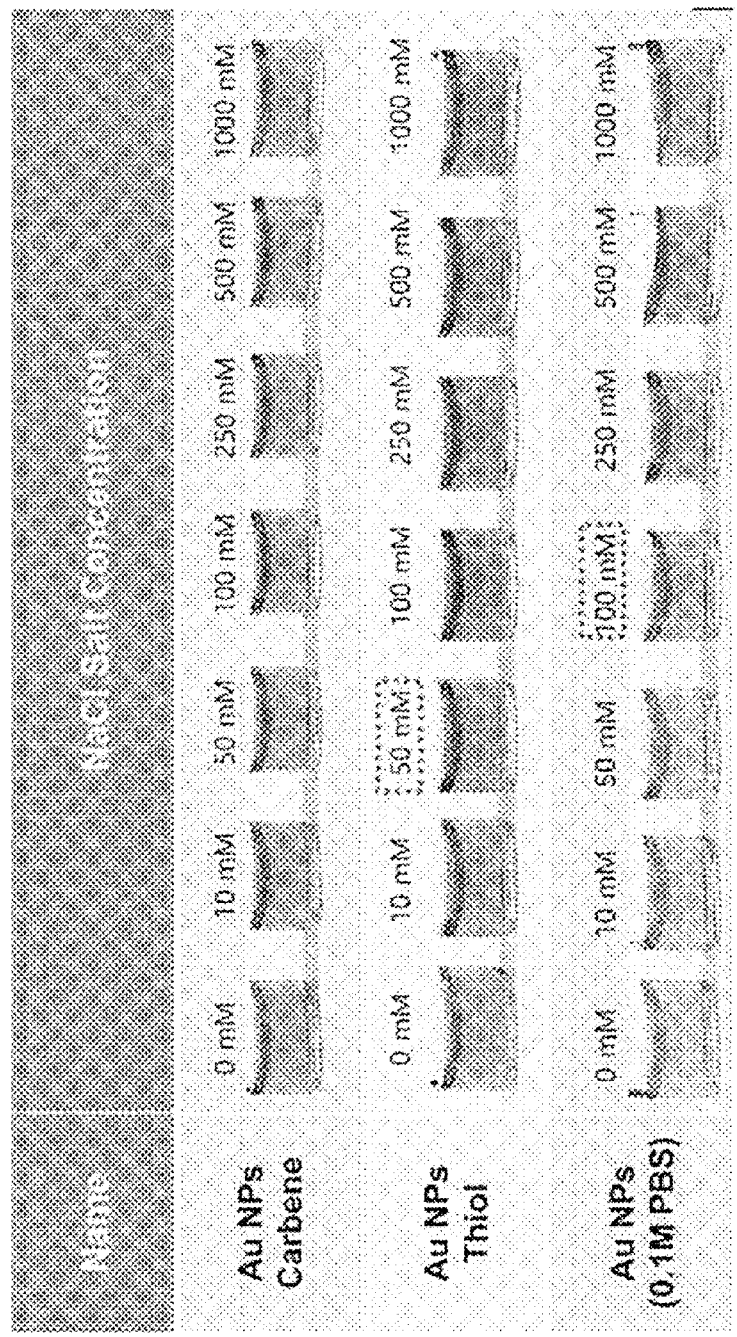
FIG. 3 is a diagram illustrating an experimental result of salt stability according to Experimental Example 2<1> of the present invention.

<1> Aqueous solutions of water and NaCl of concentrations of 10 mM, 50 mM, 100 mM, 250 mM, 500 mM, and 1,000 mM were prepared, respectively, and added with the carbene-gold nanoparticle complex (Au NPs Carbene) and the gold nanoparticle complex (Au NPs Thiol) of Example 1, and then changes in colors of the solutions were observed, and the result was shown in FIG. 3.

Figure 4:
FIG. 4 is a diagram illustrating an experimental result of solvent stability according to Experimental Example 2<2> of the present invention.
Figure 4:

<2> To confirm the stability in a high-concentration salt ion aqueous solution, the NaCl aqueous solution of 1,000 mM was added with the carbene-gold nanoparticle complex (Au NPs Carbene) of Example 1 and the gold nanoparticle complex of Comparative Example 2, and then changes in colors of the solution were observed, and the result was shown in FIG. 4.

<Experimental Example 3> Temperature Stability Experiment

Figure 5:
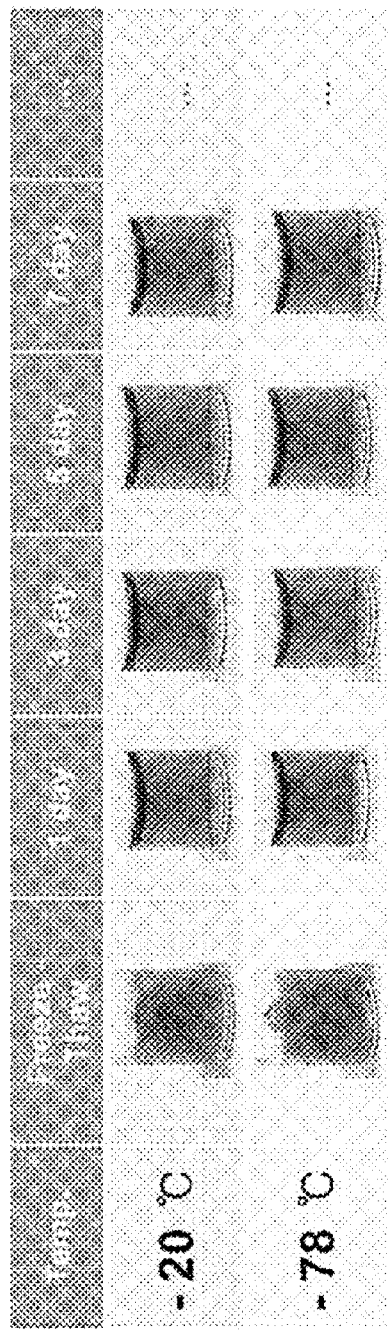
FIG. 5 is a diagram illustrating an experimental result of temperature stability according to Experimental Example 3 <1> of the present invention.

<1> Aqueous solutions of low temperature of −20° C. and ultra low temperature of −78° C. in which the carbene-gold nanoparticle complex (Au NPs Carbene) was mixed were prepared, left at room temperature, and then changes in colors of the solutions were observed after 1 day, 3 days, 5 days, and 7 days, and the result thereof was shown in FIG. 5.

Figure 6:
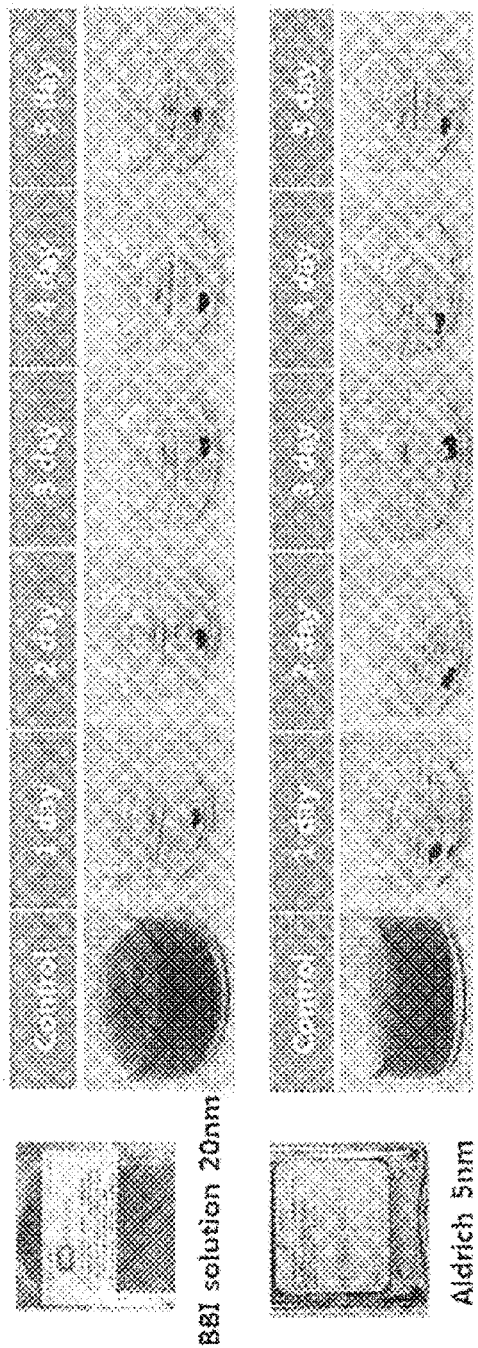
FIG. 6 is a diagram illustrating an experimental result of temperature stability of gold nanoparticles according to Experimental Example 3<2> of the present invention.

<2> Aqueous solutions were prepared by preparing 5 nm of gold nanoparticles (Aldrich) and 20 nm of gold nanoparticles (BBI solution) and then frozen to −20° C., respectively, and left at room temperature for 5 days again, and changes in aqueous solutions were observed, and the result was shown in FIG. 6.

<Experimental Example 4> Malaria Diagnostic Kit

A malaria antibody was introduced into the carbene-gold nanoparticle complex (Au NPs Carbene) in Example 1 to prepare a malaria diagnostic kit (LFA).

Figure 7:
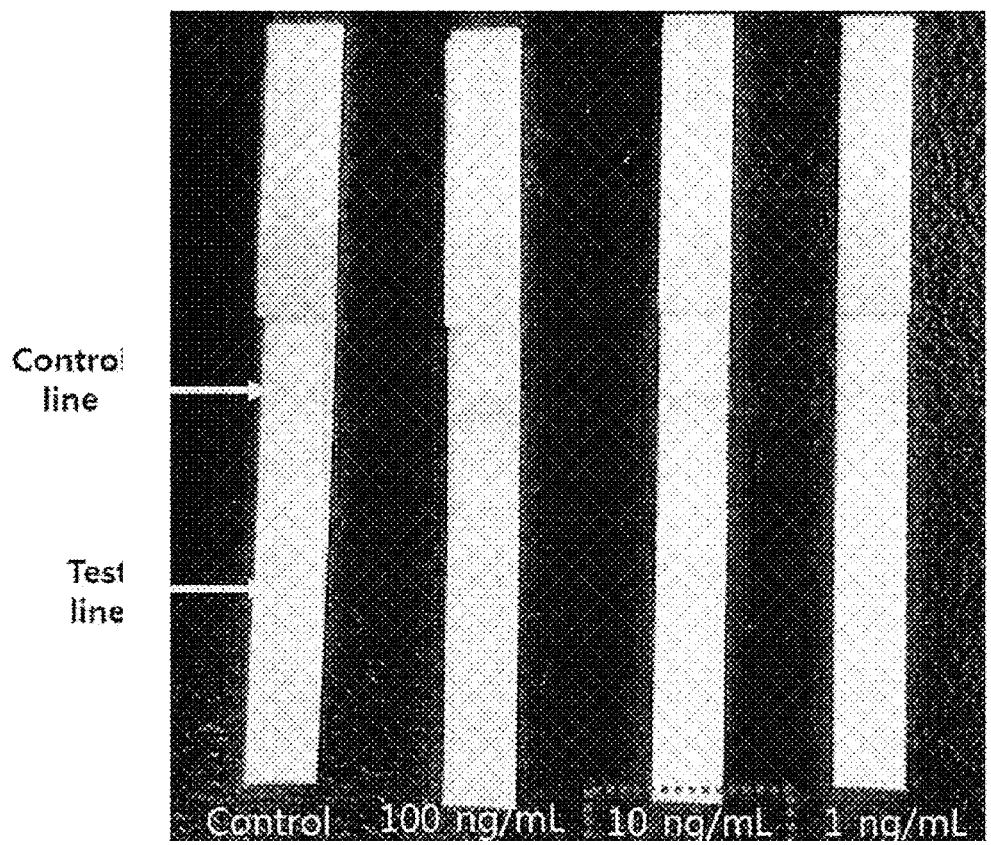
FIG. 7 is a diagram illustrating an experimental result of a malaria diagnostic kit according to Experimental Example 4 of the present invention.

A diagnostic test was performed with 100 ng/ml, 10 ng/ml, and 1 ng/ml of malaria antigen samples and the result was shown in FIG. 7.

<Experimental Example 5> pH Stability Experiment

Figure 8:
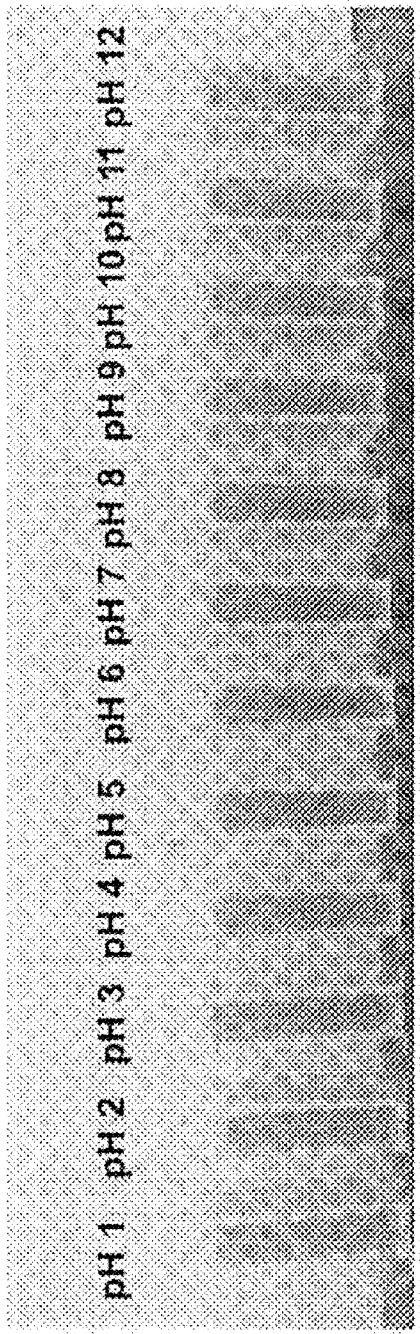
FIG. 8 is a diagram illustrating an experimental result of pH stability according to Experimental Example 5 of the present invention.
Figure 8:
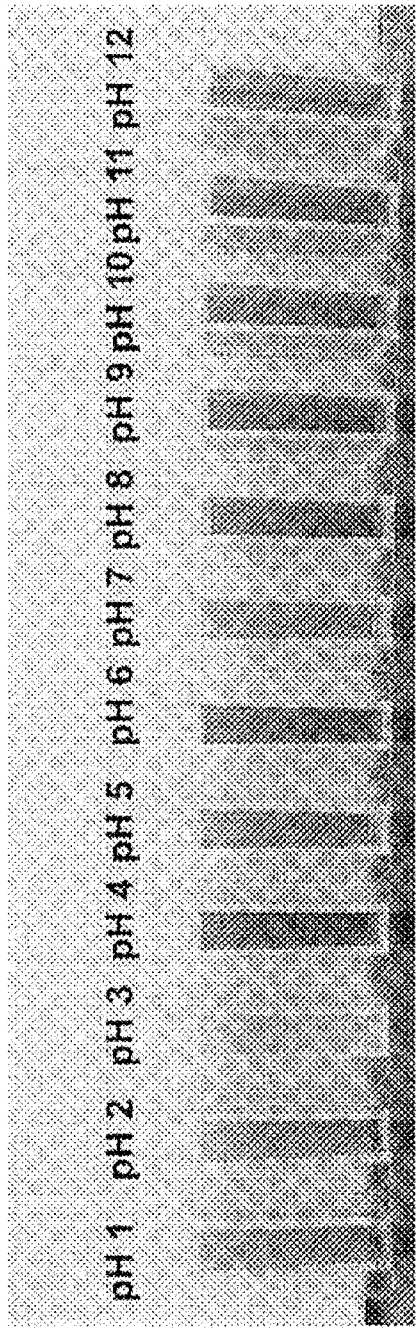

Solutions of pH 1 to 12 were prepared, respectively, and added with the carbene-gold nanoparticle complex (Au NPs Carbene) of Example 1 and the gold nanoparticle complex of Comparative Example 1, and changes in colors of the solutions were observed, and the result was shown in FIG. 8.

<Experimental Example 6> High-Temperature Stability Experiment

Figure 9:
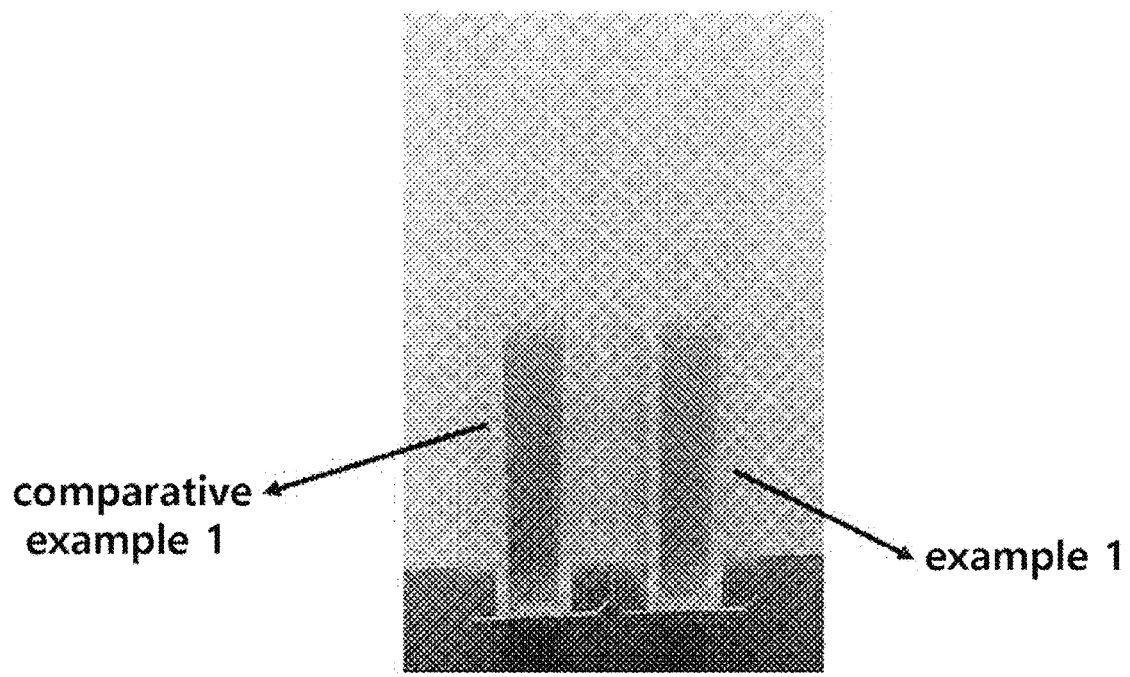
FIG. 9 is a diagram illustrating an experimental result of high-temperature stability according to Experimental Example 6 of the present invention.

Aqueous solutions added with the carbene-gold nanoparticle complex (Au NPs Carbene) of Example 1 and the gold nanoparticle complex of Comparative Example 1 were prepared, respectively, and left at 100° C. for 6 hours, and then changes in colors of the solutions were observed, and the result was shown in FIG. 9.

<Experimental Example 7> Low-Temperature Stability Experiment

Figure 10:
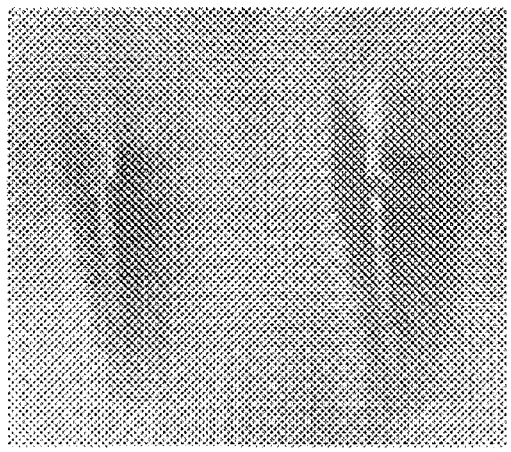
FIG. 10 is a diagram illustrating an experimental result of low-temperature stability according to Experimental Example 7 of the present invention.
Figure 10:
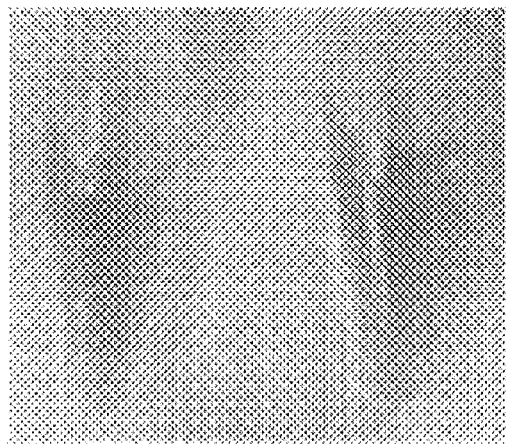

Aqueous solutions added with the carbene-gold nanoparticle complex (Au NPs Carbene) of Example 1 and the gold nanoparticle complex of Comparative Example 1 were prepared, respectively, and left at −20° C. for 6 hours, and then changes in colors of the solutions were observed, and the result was shown in FIG. 10.

According to Experimental Examples 1 and 5, the gold nanoparticles (Au NPs Thiol) bound with the thiol-PEG and the gold nanoparticles (Au NPs) showed purple (indicated by a dotted square in FIG. 2) due to the agglomeration of the gold nanoparticles because ligands bound to the gold nanoparticles were separated under a strong acid (about pH 1-3) or strong base (about pH 12) condition. On the other hand, in the carbene-gold nanoparticle complex (Au NPs Carbene) according to the present invention, it was confirmed that the gold nanoparticles were not agglomerated but stably maintained in the entire range of pH (there was no color change in the entire range of pH). In addition, according to FIG. 8, in the case of the gold nanoparticle composite of Comparative Example 1, it was confirmed that the gold nanoparticles were agglomerated under strong acid conditions (pH 1 to 3), indicating a purple color.

According to Experimental Examples 2<1> and <2>, the gold nanoparticles (Au NPs Thiol) bound with the thiol-PEG and the gold nanoparticles (Au NPs) showed dark red due to the agglomeration of the gold nanoparticles because ligands bound to the gold nanoparticles were separated around concentrations of 50 mM and 100 mM, respectively (gradually from dark red to purple). On the other hand, in the carbene-gold nanoparticle complex (Au NPs Carbene) according to the present invention, it was confirmed that the gold nanoparticles were not agglomerated but stably maintained in the entire concentration range (0 to 1,000 mM) of NaCl salt (no color changed).

According to Experimental Examples 3<1>, 6, and 7, the gold nanoparticles introduced by gold-sulfur bonds showed purple due to the agglomeration of the gold nanoparticles because ligands bound to the gold nanoparticles were separated at high temperature (70° C.) and low temperature (−20° C.). On the other hand, in the carbene-gold nanoparticle complex (Au NPs Carbene) according to the present invention, it was confirmed that the gold nanoparticles were not agglomerated but stably maintained even in high temperature (70° C.), low temperature (−20° C.), and ultra low temperature (−78° C.) (no color changed).

Meanwhile, according to Experimental Example 3<2>, in the case of gold nanoparticles as a control group, it was confirmed that the gold nanoparticles were agglomerated and precipitated in water within a few hours at low temperature (−20° C.)

According to Experimental Example 4, as shown in FIG. 7, in the malaria diagnostic kit applied with the carbene-gold nanoparticle complex (Au NPs Carbene) according to the present invention, it was confirmed that the diagnosis was enabled by finding that the Control line and Test line were observed even at a low concentration of 10 ng/ml.

The invention claimed is:

1. A carbene-metal nanoparticle complex in which a carbene compound binds to metal nanoparticles,
   wherein the carbene compound represented by the following Chemical Formula 1 or 2 substituted with polyethylene glycol (PEG) having nitrogen-containing functional groups at a terminal:

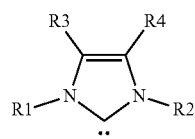

[Chemical Formula 1]

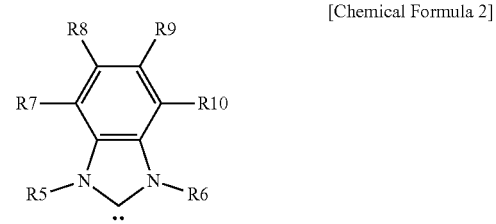

[Chemical Formula 2]

wherein Chemical Formulas 1 and 2 above,
   R1, R2, R5 and R6 are equal to or different from each other, and each independently hydrogen, an alkyl group having 1 to 20 carbon atoms, a cycloalkyl group having 3 to 20 carbon atoms, an aryl group having 6 to 30 carbon atoms, or a heteroaryl group having 2 to 30 carbon atoms,
   R3, R4, R7, R8, R9 and R10 are equal to or different from each other, and each independently hydrogen, an alkyl group having 1 to 20 carbon atoms, a cycloalkyl group having 3 to 20 carbon atoms, an aryl group having 6 to 30 carbon atoms, a heteroaryl group having 2 to 30 carbon atoms, or a structure represented by the following Chemical Formula 3, or two or more substituents adjacent to each other in R7 to R10 bind to form a hydrocarbon ring,
   at least one of R3 and R4 has a structure represented by the following Chemical Formula 3,
   at least one of R7 to R10 is a structure represented by the following Chemical Formula 3, or when two or more substituents adjacent to each other in R7 to R10 bind to form the hydrocarbon ring, at least one of hydrogens bound to carbons forming the hydrocarbon ring is substituted with a structure represented by the following Chemical Formula 3,

[Chemical Formula 3]

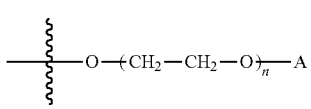

in Chemical Formula 3 above, n is an integer of 1 to 30 as a number of repeated units in parentheses, and A is an alkyl group having 1 to 20 carbon atoms containing nitrogen (N) atoms or a heteroaryl group having 2 to 30 carbon atoms containing nitrogen (N) atoms.

2. The carbene-metal nanoparticle complex of claim 1, wherein the nitrogen-containing functional group is at least one selected from the group consisting of azide, phthalimide and amine.

3. The carbene-metal nanoparticle complex of claim 1, wherein at least one of the R1 and R2 and at least one of the R5 and R6 are equal to or different from each other, and each independently an alkyl group having 1 to 20 carbon atoms, a cycloalkyl group of 3 to 20 carbon atoms, an aryl group having 6 to 30 carbon atoms, or a heteroaryl group of 2 to 30 carbon atoms.

4. The carbene-metal nanoparticle complex of claim 1, wherein a particle size of a metal nanoparticle is 1 nm to 40 nm.

5. The carbene-metal nanoparticle complex of claim 1, wherein a metal of a metal nanoparticle is any one selected from the group consisting of copper (Cu), cobalt (Co), bismuth (Bi), silver (Ag), aluminum (Al), gold (Au), hafnium (Hf), chromium (Cr), indium (In), manganese (Mn), molybdenum (Mo), magnesium (Mg), nickel (Ni), niobium (Nb), lead (Pb), palladium (Pd), platinum (Pt), rhenium (Re), rhodium (Rh), antimony (Sb), tantalum (Ta), titanium (Ti), tungsten (W), vanadium (V), zirconium (Zr), zinc (Zn), iron (Fe), and mixtures thereof.

6. A preparation method of a carbene-metal nanoparticle complex of claim 1, comprising:
preparing sulfur-metal nanoparticles by mixing polyethylene glycol containing a thiol group at one terminal and a nitrogen-containing functional group at an other terminal with metal nanoparticles; and
mixing the sulfur-metal nanoparticles with a carbene compound,
wherein the carbene compound represented by the following Chemical Formula 1 or 2 substituted with polyethylene glycol (PEG) having nitrogen-containing functional groups at a terminal:

[Chemical Formula 1]

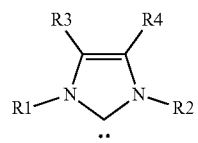

[Chemical Formula 2]

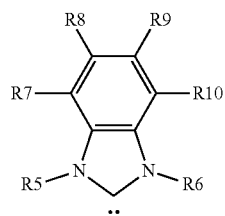

wherein Chemical Formulas 1 and 2 above,

R1, R2, R5 and R6 are equal to or different from each other, and each independently hydrogen, an alkyl group having 1 to 20 carbon atoms, a cycloalkyl group having 3 to 20 carbon atoms, an aryl group having 6 to 30 carbon atoms, or a heteroaryl group having 2 to 30 carbon atoms, R3, R4, R7, R8, R9 and R10 are equal to or different from each other, and each independently hydrogen, an alkyl group having 1 to 20 carbon atoms, a cycloalkyl group having 3 to 20 carbon atoms, an aryl group having 6 to 30 carbon atoms, a heteroaryl group having 2 to 30 carbon atoms, or a structure represented by the following Chemical Formula 3, or two or more substituents adjacent to each other in R7 to R10 bind to form a hydrocarbon ring, at least one of R3 and R4 has a structure represented by the following Chemical Formula 3, at least one of R7 to R10 is a structure represented by the following Chemical Formula 3, or when two or more substituents adjacent to each other in R7 to R10 bind to form the hydrocarbon ring, at least one of hydrogens bound to carbons forming the hydrocarbon ring is substituted with a structure represented by the following Chemical Formula 3,

[Chemical Formula 3]

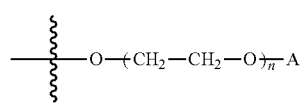

in Chemical Formula 3 above, n is an integer of 1 to 30 as a number of repeated units in parentheses, and A is an alkyl group having 1 to 20 carbon atoms containing nitrogen (N) atoms or a heteroaryl group having 2 to 30 carbon atoms containing nitrogen (N) atoms.

7. The preparation method of the carbene-metal nanoparticle complex of claim 6, wherein the mixing of the sulfur-metal nanoparticles with the carbene compound comprises substituting metal-sulfur bonds present on surfaces of the metal nanoparticles with metal-carbene bonds.

8. A biosensor comprising the carbene-metal nanoparticle complex according to claim 1 to which a bio-probe part is immobilized through a click reaction.

* * * * *